US007939554B2

(12) United States Patent (10) Patent No.: US 7,939,554 B2
Yi (45) Date of Patent: May 10, 2011

(54) PROTEIN PHOSPHATASE INHIBITORS

(75) Inventor: Taolin Yi, Solon, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 42 days.

(21) Appl. No.: 11/823,498

(22) Filed: Jun. 28, 2007

(65) Prior Publication Data

US 2008/0103160 A1 May 1, 2008

Related U.S. Application Data

(60) Provisional application No. 60/817,017, filed on Jun. 28, 2006.

(51) Int. Cl.
*A61K 31/425* (2006.01)
(52) U.S. Cl. .................................. 514/372; 514/373
(58) Field of Classification Search .................. 514/372, 514/373
See application file for complete search history.

(56) References Cited

U.S. PATENT DOCUMENTS

| 4,336,381 A | 6/1982 | Nagata et al. |
| 5,391,723 A | 2/1995 | Priest |

FOREIGN PATENT DOCUMENTS

| CN | 1513828 A | 7/2004 |
| WO | WO 99/46236 | 9/1999 |
| WO | WO 03/078959 A2 | 9/2003 |
| WO | WO 2006/047162 A2 | 5/2006 |

OTHER PUBLICATIONS

Hayakawa et al. (Biochemistry, vol. 38, No. 35, pp. 11501-11507; 1999).*
Khalaj et al. (European Journal of Medicinal Chemistry; vol. 39, pp. 699-705; 2004).*
Voskoglou-Nomikos et al. (Clinical Cancer Research, vol. 9, pp. 4227-4239; 2003).*
Galinsky et al. ["Basic Pharmacokinetics and Pharmacodynamics." in: Remington: The Science and Practice of Pharmacy (Baltimore, Lippincott Williams & Wilkins, 2006), p. 1171.].*
Abraham et al., "Jurkat T Cells and Development of the T-Cell Receptor Signalling Paradigm", *Nat. Rev. Immunol.*, 4:301-308 (2004) (Abstract Only).
Aguado et al., "Activation of T Lymphocytes and the Role of the Adapter LAT", *Transpl. Immunol.*, 17:23-26 (2006) (Abstract Only).
Araki et al., "Mouse Model of Noonan Syndrome Reveals Cell Type- and Gene Dosage-Dependent Effects of Ptpn11 Mutation", *Nat. Med.*, 10:849-857 (2004) (Abstract Only).
Aslakson et al., "Selective Events in the Metastatic Process Defined by Analysis of the Sequential Dissemination of Subpopulations of a Mouse Mammary Tumor", *Cancer Res.*, 52:1399-1405 (1992) (Full Text).
Beauchamp et al. "Proglumide, A Gastrin Receptor Antagonist, Inhibits Growth of Colon Cancer and Enhances Survival in Mice", *Ann. Surg.*, 202:303-309 (1985) (Full Text).
Becker, "Molecular Immunological Approaches to Biotherapy of Human Cancers—a Review, Hypothesis and Implications", *Anticancer Res.*, 26:1113-1134 (2006) (Abstract Only).

Berman, "Chemotherapy for Leishmaniasis:Biochemical Mechanisms, Clinical Efficacy, and Future Strategies", *Rev. Infect. Dis.*, 10:560-586 (1998) (Abstract Only).
Berman et al., "Gastrointestinal Stromal Tumor Workshop", *Hum. Pathol.*, 32:578-582 (2001) (Abstract Only).
Binstadt et al., "SLP-76 is a Direct Substrate of SHP-1 Recruited to Killer Cell Inhibitory Receptors", *J. of Biol. Chem.*, 273:27518-27523 (1998) (Full Text).
Calvelli et al., "Leukocyte Subpopulations Elicited by a Nontumorigenic Variant of B16 Melanoma: Their Role in Direct Rejection of the Melanoma and in Prevention of Tumorigenesis in Winn Assays", *J. Exp. Med.*, 156:1723-1738 (1982) (Abstract Only).
Carlomagno et al., "BAY 43-9006 Inhibition of Oncogenic RET Mutants", *J. Natl. Cancer Inst.*, 98:326-334 (2006) (Full Text).
Chiang et al., "Specific Dephosphorylation of the Lck Tyrosine Protein Kinase at Tyr-394 by the SHP-1 Protein-Tyrosine Phosphatase", *J. of Biol. Chem.*, 276:23173-23178 (2001) (Full Text).
David et al., "Differential Regulation of the Alpha/Beta Interferon-Stimulated Jak/Stat Pathway by the SH2 Domain-Containing Tyrosine Phosphatase SHPTP1", *Mol. Cell Biol.*, 15:7050-7058 (1995) (Full Text).
de Jonge et al., "Multiple Targeted Tyrosine Kinase Inhibition in the Clinic: All for One or One for All?", *Eur. J. Cancer*, 42:1351-1356 (2006) (Abstract Only).
Di Francesco et al., "Synthesis and Biological Evaluation of Novel Diaziridinylquinone-Acridine Conjugates", *Anti-Cancer Drugs*, 14:601-615 (2003) (Full Text).
Di Francesco et al., "The Abnormal Cytotoxicities of 2,5-Diaziridinyl-1,4-Benzoquinone-3-Phenyl Esters", *Anti-Cancer Drug Design*, 15:347-359 (2000), (Full Text).
Druker, "Imatinib as a Paradigm of Targeted Therapies", *Adv. Cancer Res.*, 91:1-30 (2004) (Abstract Only).
Druker, "Molecularly Targeted Therapy: Have the Floodgates Opened?", *The Oncologist*, 9:357-360 (2004) (Full Text).
Easty et al., "Protein Tyrosine Phosphatases, New Targets for Cancer Therapy", *Curr. Cancer Drug Targets*, 6:519-532 (2006) (Abstract Only).
Fan et al., "Sodium Stibogluconate Interacts with IL-2 in Anti-Renca Tumor Action via a T Cell-Dependent Mechanism in Connection with Induction of Tumor-Infiltrating Macrophages", *J. of Immunol.*, 175:7003-7008 (2005) (Full Text). Farooq et al., "Structure and Regulation of MAPK Phosphatases", *Cell Signal*, 16:769-779 (2004) (Abstract Only).
Fragale et al., "Noonan Syndrome-Associated SHP2/PTPN11 Mutants Cause EGF-Dependent Prolonged GAB1 Binding and Sustained ERK2/MAPK1 Activation", *Hum. Mutat.*, 23:267-277 (2004) (Abstract Only).
Fourie et al., "Structure-Activity Study with Bioreductive Benzoquinone Alkylating Agents: Effects on DT-Diaphorase-Mediated DNA Crosslink and Strand Break Formation in Relation to Mechanisms of Cytotoxicity", *Cancer Chemother Pharmacol*, 53:191-203 (2004) (Full Text).
Gerke et al., "The Adaptor Molecules LAT and SLP-76 are Specifcially Targeted by *Yersinia* to Inhibit T Cell Activation", *J. Exp.Med.*, 201:361-371 (2005) (Full Article).
Koon et al., "Update on Therapy for Melanoma: Opportunities for Patient Selection and Overcoming Tumor Resistance", *Expert Rev. Anticancer Ther.*, 7:79-88 (2007) (Abstract Only).
Le Lain et al., "Inhibitors of Human and Rat Testes Microsomal 17β-Hydroxysteroid Dehydrogenase (17β-HSD) as Potential Agents for Prostatic Cancer", *J. Enzyme Inhibition*, 16:35-45 (2001) (Full Text).

*Primary Examiner* — Raymond J Henley, III
(74) *Attorney, Agent, or Firm* — Tarolli, Sundheim, Covell & Tummino LLP

(57) ABSTRACT

A method of inhibiting protein tyrosine phosphatase in a subject includes administering to the subject a therapeutically effective amount of at least one benzo-1,4-quinone, phenyl isothiazolone, or analog thereof to the subject.

8 Claims, 14 Drawing Sheets

OTHER PUBLICATIONS

Lehmann et al., "The Capacity to Produce IFN-Gamma Rather than the Presence of Interleukin-4 Determines the Resistance and the Degree of Susceptibility to Leishmania Donovani Infection in Mice", *J. Interferon Cytokine Res.*, 20:63-77 (2000) (Abstract Only).

Li et al., "Efficacy of SSG and SSG/IFNalpha2 Against Human Prostate Cancer Xenograft Tumors in Mice: A Role for Direct Growth Inhibition in SSG Anti-Tumor Action", *Cancer Chemother. Pharmacol.*, (2006) (Abstract Only).

Liang et al., "Expression, Purification, and Crystallization of the Catalytic Domain of Protein Tyrosine Phosphatase SHP-1", *J. Struct. Biol.*, 120:201-203 (1997) (Abstract Only).

Lin et al., Potential Bioreductive Alkylating Agents. 5. Antineoplastic Activity of Quinoline-5,8-Diones, Naphthazarins, and Naphthoquinones, *J. of Medicinal Chem.*, 18:917-921 (1975) (Full Text).

Lin et al., Potential Bioreductive Alkylating Agents. 7. Antitumor Effects of Phenyl-Substituted 2-Chloromethyl-3-Phenyl-1,4-Napthoquinones, *J. of Medicinal Chem.*, 19:1336-1338 (1976) (Full Text).

Lindner et al., "Synergistic Antitumor Effects of a Combination of Interferons and Retinoic Acid on Human Tumor Cells in Vitro and in Vivo", *Clin. Cancer Res.*, 3:931-937 (1997) (Full Text).

Mandl et al., "Specific Inactivation and Nuclear Anchoring of Extracellular Signal-Regulated Kinase 2 by the Inducible Dual-Specificity Protein Phosphatase DUSP5", *Mol. and Cell. Biol.*, 25:1830-1845 (2005) (Full Text).

Mickey et al., "Heterotransplantation of a Human Prostatic Adenocarcinoma Cell Line in Nude Mice", *Cancer Res.*, 37:4049-4058 (1977) (Full Text).

Migone et al., "Recruitment of SH2-Containing Protein Tyrosine Phosphatase SHP-1 to the Interleukin 2 Receptor; Loss of SHP-1 Expression in Human T-Lymphotropic Virus Type I-Transformed T Cells", *Proc. Natl. Acad. Sci.*, 95:3845-3850 (1998) (Full Text).

Million et al., "Synthesis and Biological Evaluation of a New Series of Phenylhydroquinone Derivatives as Inhibitors of EGF-R-Associated PTK Activity", *Anti-Cancer Drug Design*, 11:129-153 (1996) (Full Text).

Montoya et al., "A Fluorescence-Based Rapid Screening Assay for Cytotoxic Compounds", *Biochemical and Biophysical Research Communications*, 325:1517-1523 (2004) (Full Text).

Moon et al., "Modulation of TCR Signaling by Beta1 Integrins: Role of the Tyrosine Phosphatase SHP", *Eur. J. Immunol.*, 29:3887-3897 (1999) (Abstract Only).

Motzer et al. "Sunitinib in Patients with Metastatic Renal Cell Carcinoma", *Jama*, 295:2516-2524 (2006) (Abstract Only).

Muranski et al., "Increased Intensity Lymphodepletion and Adoptive Immunotherapy-How Far Can We Go?", *Nat. Clin. Pract. Oncol.*, 3:668-681 (2006) (Full Text).

Murray et al., "SU11248 Inhibits Tumor Growth and CSF-1R-Dependent Osteolysis in an Experimental Breast Cancer Bone Metastasis Model", *Clin. Exp. Metastasis*, 20:757-766 (2003) (Abstract Only).

Murray et al. "Advances in Leishmaniasis", *Lancet*, 366:1561-1577 (2005) (Abstract Only).

Parton et al. "Role of Cytokine Therapy in 2006 and Beyond for Metastatic Renal Cell Cancer", *J. of Clin. Oncol.*, 24:5584-5592 (2006) (Abstract Only).

Pathak et al., "Sodium Stibogluconate is a Potent Inhibitor of Protein Tyrosine Phosphatases and Augments Cytokine Responses in Hemopoietic Cell Lines", *J. Immunol.*, 167:3391-3397 (2001) (Full Text).

Pathak et al., "Effects of Sodium Stibogluconate on Differentiation and Proliferation of Human Myeloid Leukemia Cell Lines in Vitro", *Leukemia*, 16:2285-2291 (2002) (Full Text).

Plas et al., "Direct Regulation of ZAP-70 by SHP-1 in T Cell Antigen Receptor Signaling", *Science*, 272:1173-1176 (1996) (Abstract Only).

Puder et al., "Terphenylquinone Inhibitors of the Src Protein Tyrosine Kinase from *Stilbella sp.*", *J. Nat. Prod.*, 68:323-326 (2005) (Full Text).

Saha et al. "A Phosphatase Associated with Metastasis of Colorectal Cancer", *Science*, 294:1343-1346 (2001) (Full Text).

Sarfaraz et al. "Cannabinoid Receptor Agonist-Induced Apoptosis of Human Prostate Cancer Cells LNCaP Proceeds Through Sustained Activation of ERK 1/2 Leading to $G_1$ Cell Cycle Arrest", *J. of Biol. Chem.*, 281:39480-39491 (2006) (Full Text).

Schneider et al., "Characterization of EBV-Genome Negative "Null" and "T" Cell Lines Derived from Children with Acute Lymphoblastic Leukemia and Leukemic Transformed Non-Hodgkin Lymphoma", *Int. J. Cancer*, 19:621-626 (1977) (Abstract Only).

Shi et al., "The Shp-2 Tyrosine Phosphatase has Opposite Effects in Mediating the Activation of Extracellular Signal-Regulated and c-Jun $NH_2$-Terminal Mitrogen-Activated Protein Kinases", *J. of Biol. Chem.*, 273:4904-4908 (1998) (Full Text).

Shultz et al., "Mutations at the Murine Motheaten Locus are within the Hematopoietic Cell Protein-Tyrosine Phosphatase (Hcph) Gene", *Cell*, 73:1445-1454 (1993) (Abstract Only).

Sieh et al., "CD45 Specifically Modulates Binding of Lck to a Phosphopeptide Encompassing the Negative Regulatory Tyrosine of Lck", *EMBO J.*, 12:315-321 (1993) (Full Text).

Talmadge et al., "Role of Natural Killer Cells in Tumor Growth and Metastasis: C57BL/6 Normal and Beige Mice", *J. Natl Cancer Inst.*, 65:929-935 (1980) (Abstract Only).

Tartaglia et al., "Mutations in PTPN11, Encoding the Protein Tyrosine Phosphatase SHP-2, Cause Noonan Syndrome", *Nat. Genet.*, 29:465-468 (2001) (Abstract Only).

Tartaglia et al., "PTPN11 Mutations in Noonan Syndrome: Molecular Spectrum, Genotype-Phenotype Correlation, and Phenotypic Heterogeneity", *Am. J. Hum. Genet*, 70:1555-1563 (2002) (Full Text).

Tartaglia et al., "Somatic Mutations in PTPN11 in Juvenile Myelomonocytic Leukemia, Myelodysplastic Syndromes and Acute Myeloid Leukemia", *Nat. Genet.*, 34:148-150 (2003) (Abstract Only).

Tartaglia et al., "SHP-2 and Myeloid Malignancies", *Curr. Opin. Hematol.*, 11:44-50 (2004) (Abstract Only).

Tartaglia et al., "Germ-Line and Somatic PTPN11 Mutations in Human Disease", *Eur. J. Med. Genet*, 48:81-96 (2005) (Abstract Only).

Tonks "Protein Tyrosine Phosphatases: from Genes, to Function, to Disease", *Nat. Rev. Mol. Cell Biol.*, 7:833-846 (2006) (Abstract Only).

Traxler et al., "4-(Phenylamino) Pyrrolopyrimidines: Potent and Selective, ATP Site Directed Inhibitors of the EGF-Receptor Protein Tyrosine Kinase", *J. Med. Chem.*, 39:2285-2292 (1996) (Abstract Only).

Wang et al. "Irofulven (6-Hydroxymethylacylfulvene, MGI 114)-Induced Apoptosis in Human Pancreatic Cancer Cells is Mediated by ERK and JNK Kinases", *Anticancer Res.*, 22:559-564 (2002) (Abstract Only).

Yang et al., "Immunotherapy for Renal Cell Cancer", *J. Clin. Oncol.*, 24:5576-5583 (2006) (Abstract Only).

Yi et al., "Association of Hematopoietic Cell Phosphatase with c-Kit after Stimulation with c-Kit Ligand", *Molecular and Cellular Biology*, 13:3350-3358 (1993) (Full Text).

Yi et al. "Hematopoietic Cell Phosphatase Associates with the Interleukin-3 (IL-3) Receptor β Chain and Down-Regulates IL-3-Induced Tyrosine Phosphorylation and Mitogenesis", *Molecular and Cellular Biology*, 13:7577-7586 (1993) (Full Text).

Yi et al. "Anticancer Activity of Sodium Stibogluconate in Synergy with IFNs[1]", *J. of Immunol.*, 169:5978-5985 (2002) (Full Text).

Yu et al., "Abnormal Th1 Differentiation and IFN-γ Production in T Lymphocytes from Motheaten Viable Mice Mutant for Src Homology 2 Domain-Containing Protein Tyrosine Phosphatase-1[1]", *J. of Immunol.*, 174:1013-1019 (2005) (Full Text).

Zhang et al. "Roles of the SHP-1 Tyrosine Phosphatase in the Negative Regulation of Cell Signalling", *Semin. Immunol.*, 12:361-378 (2000) (Abstract Only).

* cited by examiner

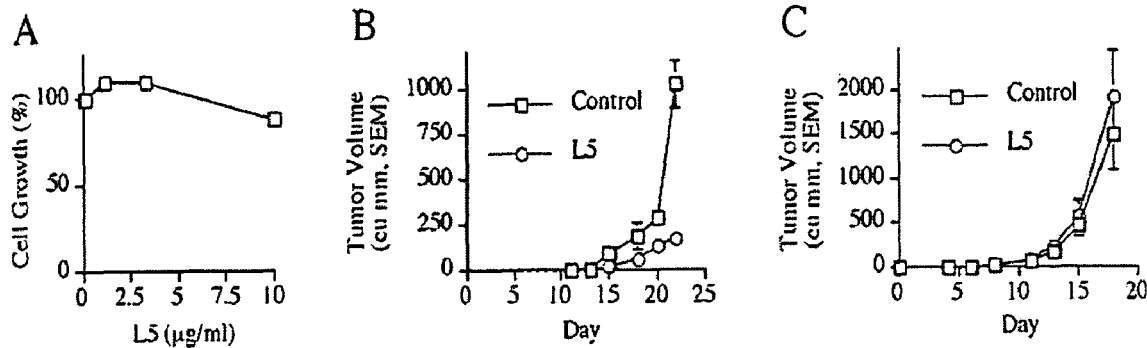

Fig. 7

Table 1

| | Targeting SHP-1 | | | | Targeting SHP-2 | | | |
|---|---|---|---|---|---|---|---|---|
| | Inhibition of rSHP-1 | Inhibition of cellular SHP-1 (pLck induction) | Induction of IFNγ+ cells in vitro | T cell-dependent α-tumor activity in mice | Inhibition of rSHP-2 | Inhibition of cellular SHP-2 (pSTAT1 induction) | Inhibition of cancer cell growth in vitro | Direct inhibition of tumor growth in mice |
| SSG | + | 10 µg/ml | 20 µg/ml | yes | + | 10 µg/ml | yes | yes |
| L5 | + | 10 ng/ml | 100 ng/ml | | + | | | |
| 5a1 | | + | | | | | | |
| 5a2 | | + | | | | | | |
| 5a3 | | + | | | | | | |
| 3a | | + | | | | | | |
| 3d | | + | | | | | | |
| 5a4 | | + | | | | | | |
| 5a5 | | + | | | | | | |

Fig. 8

PROTEIN PHOSPHATASE INHIBITORS

RELATED APPLICATION

This application claims priority from U.S. Provisional Patent Application Ser. No. 60/817,017, filed on Jun. 28, 2006, the subject matter of which is incorporated herein by reference.

TECHNICAL FIELD

The present invention relates to compounds and therapeutic agents that can be used as selective inhibitors of protein tyrosine phosphatases (PTPase), and particularly relates to protein tyrosine phosphatase inhibitors that can be used to treat neoplastic disorders.

BACKGROUND OF THE INVENTION

Intracellular protein tyrosine phosphorylation is regulated by extracellular stimuli, such as cytokines, to control cell growth, differentiation and functional activities. This signaling mechanism depends on the interplay of protein tyrosine kinases, which initiate signaling cascades through phosphorylating tyrosine residues in protein substrates, and by protein tyrosine phosphatases (PTPases) that terminate signaling via substrate dephosphorylation. Chemical compounds that modulate the activity of protein tyrosine kinases or phosphatases can induce cellular changes through affecting the balance of intracellular protein tyrosine phosphorylation and redirecting signaling.

Among the approximately one hundred PTPases encoded in the human genome, two PTPases in particular, Src homology protein tyrosine phosphatase 1 (SHP-1) and SHP-2, may be attractive targets for developing novel anti-cancer therapeutics. Based on its negative regulatory role in immune cells and cytokine signaling, SHP-1 may be inhibited by small molecules to augment anti-cancer efficacy of immunotherapy or cytokine therapy. Additionally, because SHP-2 is an oncogenic molecule in human malignancies and a mitogenic signal transducer, inhibitors of SHP-2 may also be expected to inhibit tumor cell growth.

So far, few clinically usable inhibitors of PTPases have been reported despite extensive efforts in the last decade to identify them. Although a number of chemicals that broadly inhibit PTPases are known (e.g. sodium orthovanadate, pervanadate, and iodoacetic acid), their value as therapeutic agents has been limited due to their non-selective action resulting in toxicity in vivo.

SUMMARY OF THE INVENTION

The present invention relates to a method of inhibiting protein tyrosine phosphatase in a subject by administering to the subject a therapeutically effective amount of at least one benzo-1,4-quinone or analog thereof and/or phenyl isothiazolone or analog thereof. The at least one benzo-1,4-quinone or analog there of and/or phenyl isothiazolone or analog thereof can be administered to the subject to treat neoplastic disorders and/or proliferative disorders, activate immune cells, and/or activate and or potentiate cytokine response for therapeutic treatments to the subject.

In an aspect of the invention, the at least one benzo-1,4-quinone or analog there of and/or phenyl isothiazolone or analog thereof can be administered at an amount effective to at least partially inhibit SHP-1 in the subject. The at least one benzo-1,4-quinone or analog there of and/or phenyl isothiazolone or analog thereof can also be administered at an amount effective to inhibit neoplastic cell growth in the subject. The at least one benzo-1,4-quinone or analog there of and/or phenyl isothiazolone or analog thereof can further be administered at an amount effective to induce immune cell (e.g., IFNγ+ cell) activation in the subject and/or induce or potentiate cytokine responses in the subject. In a further aspect, the at least one benzo-1,4-quinone or analog there of and/or phenyl isothiazolone or analog thereof can be administered at about 1 μg/kg to about 10 mg/kg to the subject.

In another aspect of the invention, the benzo-1,4-quinone or analog thereof can comprise the formula (I):

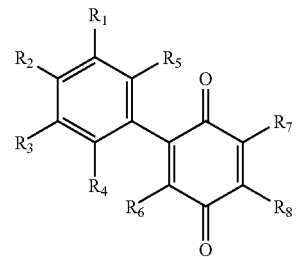

where $R_1$, $R_2$, $R_3$, $R_4$, $R_5$, $R_6$, $R_7$, and $R_8$ each independently represent substituents selected from the group consisting of hydrogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, $C_2$-$C_{24}$ alkylcarbonyl (—CO-alkyl), $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO⁻), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano(—CN), isocyano (—N⁺C⁻), cyanato (—O—CN), isocyanato (—O—N⁺=C⁻), isothiocyanato (—S—CN), azido (—N=N⁺=N⁻), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino, alkylimino, arylimino, nitro (—NO$_2$), nitroso (—NO), sulfo (—SO$_2$—OH), sulfonato (—SO$_2$—O⁻), $C_1$-$C_{24}$ alkylsulfanyl (—S-alkyl), arylsulfanyl, $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O⁻)$_2$), phosphinato (—P(O)(O⁻)), phospho (—PO$_2$), phosphino (—PH$_2$), and combinations thereof; or a pharmaceutically acceptable salt thereof.

In a further aspect, the benzo-1,4-quinone or analog thereof can comprise at least one of the following formulas:

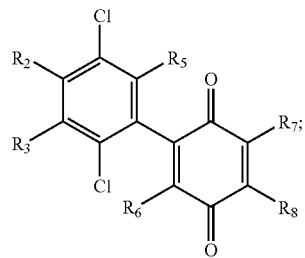
(II)

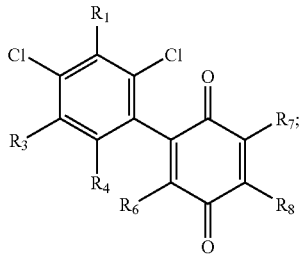
(III)

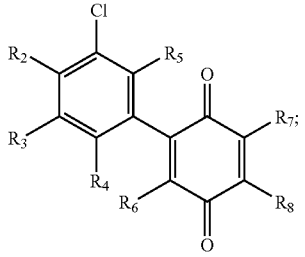
(IV)

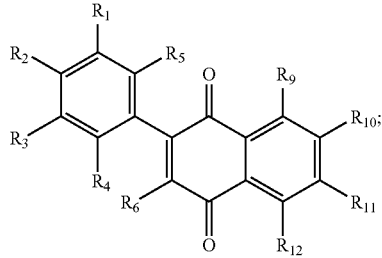
(V)

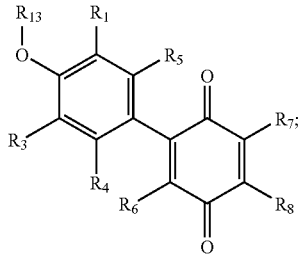
(VI)

where $R_9$, $R_{10}$, $R_{11}$, $R_{12}$, and $R_{13}$ each independently represent substituents selected from the group consisting of hydrogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, $C_2$-$C_{24}$ alkylcarbonyl (—CO-alkyl), $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ arylcarbonato (—O—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano (—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino, alkylimino, arylimino, nitro (—NO$_2$), nitroso (—NO), sulfo (—SO$_2$—OH), sulfonato (—SO$_2$—O$^-$), $C_1$-$C_{24}$ alkylsulfanyl (—S-alkyl), arylsulfanyl, $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), phosphino (—PH$_2$), and combinations thereof; or a pharmaceutically acceptable salt thereof.

In still a further aspect, the benzo-1,4-quinone can comprise at least one of the following formulas:

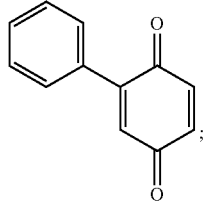
(Ia)

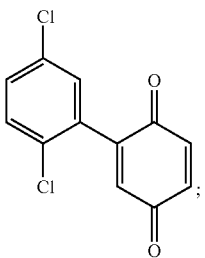
(IIa)

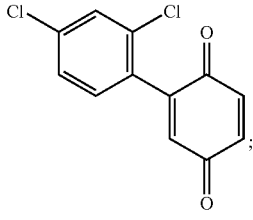
(IIIa)

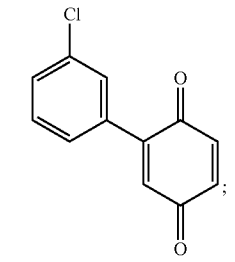
(IVa)

-continued

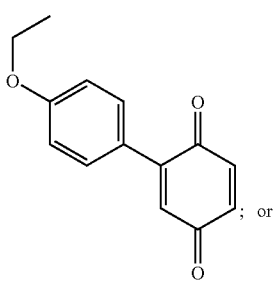
(VIa)

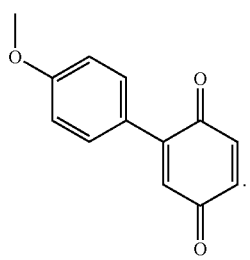
(VIb)

In another aspect of the invention, the phenyl isothiazolone or analog thereof can comprise the formula (VII):

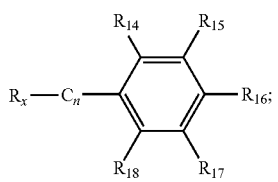
(VII)

where Rx is a isothiazolone or analog thereof comprising a heterocyclic five membered ring containing at least one nitrogen atom and sulfur atom in the ring;

n is 0 or 1;

$R_{14}$, $R_{15}$, $R_{16}$, $R_{17}$, and $R_{18}$ each independently represent substituents selected from the group consisting of hydrogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, $C_2$-$C_{24}$ alkylcarbonyl (—CO-alkyl), $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano(—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino, alkylimino, arylimino, nitro (—NO$_2$), nitroso (—NO), sulfo (—SO$_2$—OH), sulfonato (—SO$_2$—O$^-$), $C_1$-$C_{24}$ alkylsulfanyl (—S-alkyl), arylsulfanyl, $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), phosphino (—PH$_2$), and combinations thereof, or a pharmaceutically acceptable salt thereof.

In a further aspect, the phenyl isothiazolone or analog thereof can comprise at least one of the following formulas:

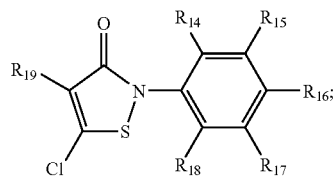
(VIII)

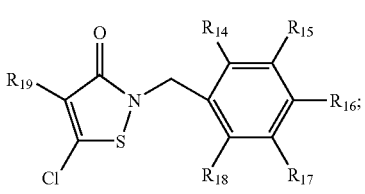
(IX)

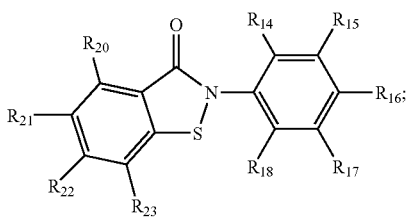
(X)

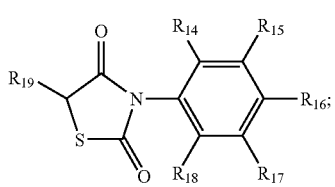
(XI)

where $R_{14}$, $R_{15}$, $R_{16}$, $R_{17}$, $R_{18}$, $R_{19}$, $R_{20}$, $R_{21}$, $R_{22}$ and $R_{23}$ each independently represent substituents selected from the group consisting of hydrogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, $C_2$-$C_{24}$ alkylcarbonyl (—CO-alkyl), $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano (—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino, alkylimino, arylimino, nitro (—NO$_2$), nitroso (—NO), sulfo (—SO$_2$—OH), sulfonato (—SO$_2$—O$^-$), C$_1$-C$_{24}$ alkylsulfanyl (—S-alkyl), arylsulfanyl, C$_1$-C$_{24}$ alkylsulfinyl (—(SO)-alkyl), C$_5$-C$_{20}$ arylsulfinyl (—(SO)-aryl), C$_1$-C$_{24}$ alkylsulfonyl (—SO$_2$-alkyl), C$_5$-C$_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), phosphino (—PH$_2$), and combinations thereof; or a pharmaceutically acceptable salt thereof.

In a still further aspect, the phenyl isothiazolone or analog thereof can comprise at least one of the following formulas:

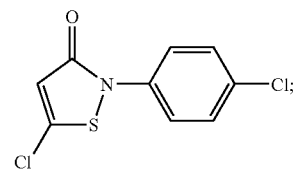
(VIIIa)

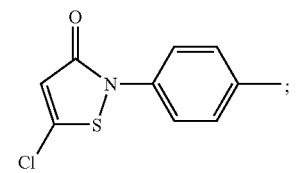
(VIIIb)

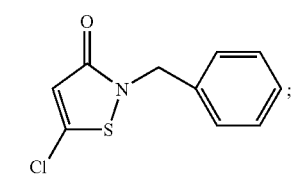
(IXa)

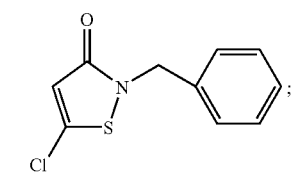
(IXa)

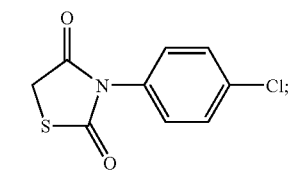
(XIa)

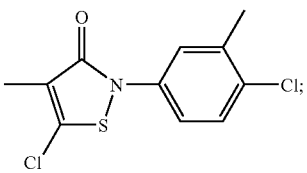
(VIIIc)

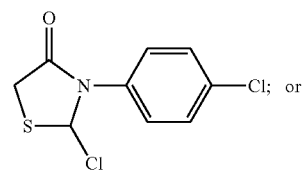
(XIIa)

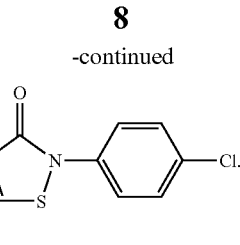
(VIIId)

BRIEF DESCRIPTION OF THE DRAWINGS

The foregoing and other features of the present invention will become apparent to those skilled in the art to which the present invention relates upon reading the following description with reference to the accompanying drawings, in which:

FIG. 7 illustrates L5 inhibits B16 melanoma tumor growth in mice but has little effects on B16 cell growth in vitro. A, Growth of B16 melanoma cells cultured in the absence or presence of L5 for 5 days was quantified by MTT assays. Data represent mean±SD of triplicate samples. B, C57BL/B6 mice bearing 4-day-established B16 melanoma tumors were treated with PBS (Control) or L5 (3 mg/kg of body weight/day, oral, M-F/week). Tumor volumes were recorded as indicated. C, Athymic nude mice bearing 4-day-established B16 tumors were subjected to differential treatments as in B. Tumor volumes were recorded as indicated.

FIG. 8 illustrates a strategy for developing L5 as a potential anti-cancer agent.

DETAILED DESCRIPTION

Figure 1:
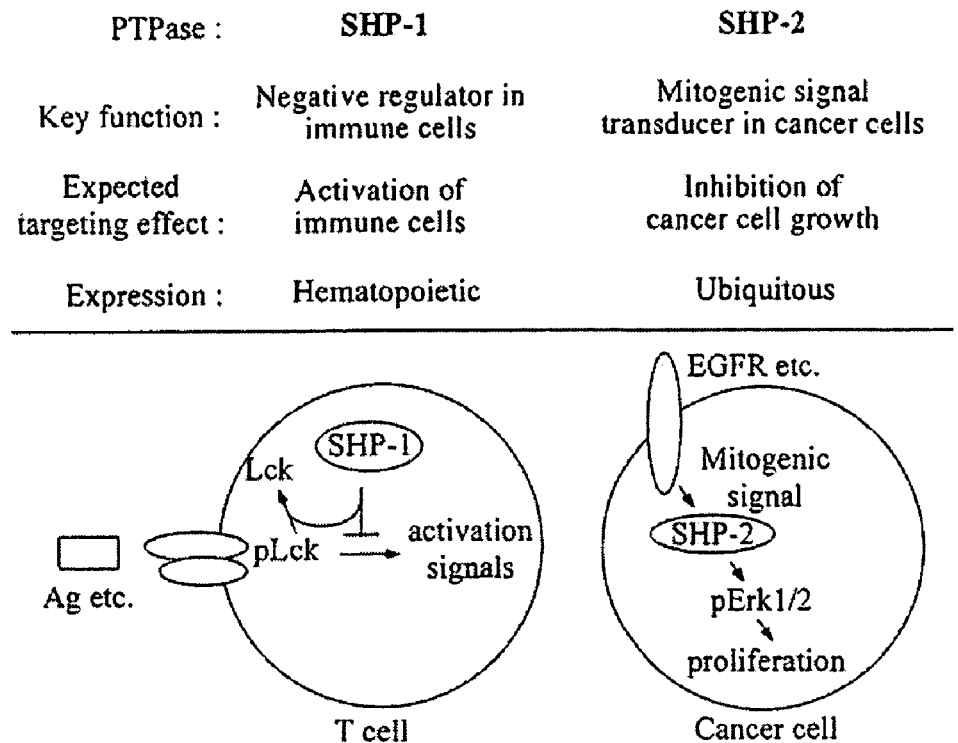
FIG. 1 is a schematic showing SHP-1 and SHP-2 as anti-cancer targets.

As used herein, the term "therapeutically effective amount" refers to that amount of a composition that results in amelioration of symptoms or a prolongation of survival in a patient. A therapeutically relevant effect relieves to some extent one or more symptoms of a disease or condition or returns to normal either partially or completely one or more physiological or biochemical parameters associated with or causative of the disease or condition.

As used herein, the terms "host" and "subject" refer to any animal, including, but not limited to, humans and non-human animals (e.g., rodents, arthropods, insects, fish (e.g., zebrafish), non-human primates, ovines, bovines, ruminants, lagomorphs, porcines, caprines, equines, canines, felines, aves, etc.), which is to be the recipient of a particular treatment. Typically, the terms "host," "patient," and "subject" are used interchangeably herein in reference to a human subject.

The term "modulate," as used herein, refers to a change in the biological activity of a biologically active molecule. Modulation can be an increase or a decrease in activity, a change in binding characteristics, or any other change in the; biological, functional, or immunological properties of biologically active molecules.

As used herein, the term "in vitro" refers to an artificial environment and to processes or reactions that occur within an artificial environment. In vitro environments consist of, but are not limited to, test tubes and cell culture. The term "in vivo" refers to the natural environment (e.g., an animal or a cell) and to processes or reaction that occur within a natural environment.

"Treating" or "treatment" of a condition or disease includes: (1) preventing at least one symptom of the conditions, i.e., causing a clinical symptom to not significantly develop in a mammal that may be exposed to or predisposed to the disease but does not yet experience or display symptoms of the disease, (2) inhibiting the disease, i.e., arresting or reducing the development of the disease or its symptoms, or (3) relieving the disease, i.e., causing regression of the disease or its clinical symptoms.

The present invention relates to methods and compositions that provide for the treatment, prevention, inhibition, and management of diseases and disorders associated with protein tyrosine phosphatase (PTPase) activation as well as to methods and assays of identifying therapeutic agents or compounds capable of inhibiting PTPases in a subject being treated. For example, the PTPase inhibitors of the present invention may be used to treat a disease or condition dependent upon substrate dephosphorylation, where selective inhibition of a PTPase, such as SHP-1, MKP-1, and/or SHP-2, would be beneficial. PTPase inhibitors in accordance with the invention have a high-potency and low toxicity in mammalian subjects and can be used as in the treatment of hyperproliferative disorders, neoplastic disorders, and disorders where an increased immune cell activation and/or cytokine response is desired.

The present invention is based at least in part on the discovery that PTPase inhibitors identified by a SFP-1 PTPase assay in accordance with the present invention when administered to a subject can inhibit neoplastic cell growth (e.g., melanoma cell growth), increase immune cell activation, and/or cytokine response in the subject. The PTPase inhibitors can therefore be used as agents for the treatment, prevention, inhibition, or management of cancers, for example, human cancers of the breast, lung, skin, prostate, bladder, and pancreas, and renal cell carcinomas and melanomas. The PTPase inhibitors can also be used to inhibit proliferation of cancer cells by suppressing activating anti-tumor immune cells in the subject as well as inhibit neoplastic cell (e.g., cancer cell) survival by inhibiting SHP-1, MKP-1, and other PTPases in accordance with the present invention.

Cancers and related disorders that can be treated, prevented, or managed by methods, PTPase inhibitors and compositions of the present invention include but are not limited to cancers include the following: leukemias, such as but not limited to, acute leukemia, acute lymphocytic leukemia, acute myelocytic leukemias, such as, myeloblastic, promyelocytic, myelomonocytic, monocytic, and erythroleukemia leukemias and myelodysplastic syndrome; chronic leukemias, such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to ductal carcinoma, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma; gallbladder cancers such as adenocarcinoma; cholangiocarcinomas such as but not limited to papillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, prostatic intraepithelial neoplasia, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell carcinoma, adenocarcinoma, hypemephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J. B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America)

PTPase inhibitors of the invention are also useful in the treatment or prevention of a variety of cancers or other abnormal proliferative diseases, including (but not limited to) the following: carcinoma, including that of the bladder, breast, prostate, rectal, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Burkitt's lymphoma; hematopoictic tumors of myeloid lineage, including acute and chronic myelogenous leukemias and promyclocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscarama, and osteosarcoma; and other tumors, including melanoma, xeroderma pigmentosum, keratoactanthoma, seminoma, thyroid follicular cancer and teratocarcinoma. It is also contemplated that cancers caused by aberrations in apoptosis would also be treated by the methods and compositions of the invention. Such cancers may include but not be limited to follicular lymphomas, carcinomas with p53 mutations, hormone dependent tumors of the breast, prostate and ovary, and pre-cancerous lesions such as familial adenomatous polyposis, and myelodysplastic syndromes. In specific embodiments, malignancy or dysproliferative changes (such as metaplasias and dysplasias), or hyperproliferative disorders, are treated or prevented in the skin, lung, colon, rectum, breast, prostate, bladder, kidney, pancreas, ovary, or uterus. In other specific embodiments, sarcoma, melanoma, or leukemia is treated or prevented.

In other embodiments, the PTPase inhibitors of the present invention can be used to treat, prevent or manage other diseases or disorders associated with cell hyperproliferation, for example but not limited to restenosis, inflammation, asthma, chronic obstructive lung diseases, psoriasis, etc. The present invention also relates to methods for the treatment, inhibition, and management of cancer or other hyperproliferative cell disorder or disease that has become partially or completely refractory to current or standard cancer treatment, such as chemotherapy, radiation therapy, hormonal therapy, and biological therapy.

In an aspect of the invention, the PTPase inhibitor can be a benzo-1,4-quinone or analog thereof have the following general formula (I):

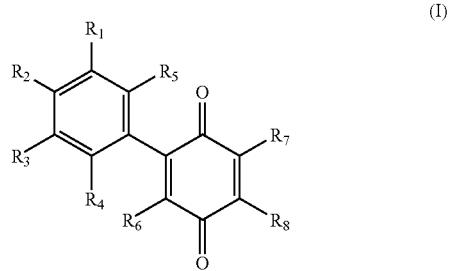

(I)

where $R_1$, $R_2$, $R_3$, $R_4$, $R_5$, $R_6$, $R_7$, and $R_8$ each independently represent substituents selected from the group consisting of hydrogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano (—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), phosphino (—PH$_2$), and combinations thereof, or a pharmaceutically acceptable salt thereof.

The term "alkyl" refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups, such as cyclopentyl, cyclohexyl, and the like. Generally, although again not necessarily, alkyl groups herein contain 1 to about 18 carbon atoms, preferably 1 to about 12 carbon atoms. The term "lower alkyl" intends an alkyl group of 1 to 6 carbon atoms. Substituents identified as "$C_1$-$C_6$ alkyl" or "lower alkyl" can contain 1 to 3 carbon atoms, and more particularly such substituents can contain 1 or 2 carbon atoms (i.e., methyl and ethyl). "Substituted alkyl" refers to alkyl substituted with one or more substituent groups, and the terms "heteroatom-containing alkyl" and "heteroalkyl" refer to alkyl in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "alkenyl" refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, cyclopentenyl, cyclohexenyl, cyclooctenyl, and the like. Generally, although again not necessarily, alkenyl groups can contain 2 to about 18 carbon atoms, and more particularly 2 to 12 carbon atoms. The term "lower alkenyl" refers to an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl or heterocycloalkenyl (e.g., heterocylcohexenyl) in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" refers to a linear or branched hydrocarbon group of 2 to 24 carbon atoms containing at least one triple bond, such as ethynyl, n-propynyl, and the like. Generally, although again not necessarily, alkynyl groups can contain 2 to about 18 carbon atoms, and more particularly can contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" refers to an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "$C_1$-$C_6$ alkoxy" or "lower alkoxy" herein contain 1 to 3 carbon atoms, and particularly preferred such substituents contain 1 or 2 carbon atoms (i.e., methoxy and ethoxy).

The term "aryl" refers to an aromatic substituent containing a single aromatic ring or multiple aromatic rings that are fused together, directly linked, or indirectly linked (such that the different aromatic rings are bound to a common group such as a methylene or ethylene moiety). Aryl groups can contain 5 to 20 carbon atoms, and particularly preferred aryl groups can contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl, in which at least one carbon atom is replaced with a heteroatom, as will be described in further detail infra. If not otherwise indicated, the term "aryl" includes unsubstituted, substituted, and/or heteroatom-containing aromatic substituents.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 20 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Exemplary aralkyl groups contain 6 to 24 carbon atoms, and particularly preferred aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like.

The term "cyclic" refers to alicyclic or aromatic substituents that may or may not be substituted and/or heteroatom containing, and that may be monocyclic, bicyclic, or polycyclic.

The terms "halo" and "halogen" are used in the conventional sense to refer to a chloro, bromo, fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g. nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

"Hydrocarbyl" refers to univalent hydrocarbyl radicals containing 1 to about 30 carbon atoms, preferably 1 to about 24 carbon atoms, more preferably 1 to about 18 carbon atoms, most preferably about 1 to 12 carbon atoms, including linear, branched, cyclic, saturated, and unsaturated species, such as alkyl groups, alkenyl groups, aryl groups, and the like. "Substituted hydrocarbyl" refers to hydrocarbyl substituted with one or more substituent groups, and the term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

By "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups such as halo, hydroxyl, silyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_4$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano(—CN), isocyano (—N$^+$C$^-$), cyanato (—O—CN), isocyanato (—ON$^+$C$^-$), isothiocyanato (—S—CN), azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl;

also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)(O$^-$)$_2$), phosphinato (—P(O)(O$^-$)), phospho (—PO$_2$), and phosphino (—PH$_2$); and the hydrocarbyl moieties $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, and $C_6$-$C_{24}$ aralkyl.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl."

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

When referring to a PTPase of the present invention, applicants intend the phrase "PTPase inhibitor" to encompass not only the specified molecular entity, but also its pharmaceutically acceptable, pharmacologically active analogs, including, but not limited to, salts, esters, amides, prodrugs, conjugates, active metabolites, and other such derivatives, analogs, and related compounds.

The term "therapeutic" refers to reduction in severity and/or frequency of symptoms, elimination of symptoms and/or underlying cause, prevention of the occurrence of symptoms and/or their underlying cause, and improvement or remediation of disease. For example, treatment of a patient by administration of a PTPase inhibitor of the present invention encompasses chemroprevention in a patient susceptible to developing cancer (e.g., at a higher risk, as a result of genetic predisposition, environmental factors, or the like) and/or in cancer survivors at risk of cancer recurrence, as well as treatment of a cancer patient by inhibiting or causing regression of a disorder or disease.

"Effective amounts", in terms of each of the foregoing methods, are amounts of the at least one PTPase inhibitor effective to modulate or inhibit PTPase activity without being cytotoxic to the patient.

Some of the PTPase inhibitors disclosed herein may contain one or more asymmetric centers and may thus give rise to enantiomers, diastereomers, and other stereoisomeric forms. The present invention is also meant to encompass racemic mixtures, resolved forms and mixtures thereof, as well as the individual enantiomers that may be separated according to methods that are well know to those of ordinary skill in the art.

When the PTPase inhibitors described herein contain olefinic double bonds or other centers of geometric asymmetry, and unless specified otherwise, it is intended to include both E and Z geometric isomers.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "asymmetric center" or "chiral center" refers to a carbon atom to which four different groups are attached.

The term "enantiomer" or "enantiomeric" refers to a molecule that is nonsuperimposeable on its mirror image and hence optically active wherein the enantiomer rotates the plane of polarized light in one direction and its mirror image rotates the plane of polarized light in the opposite direction.

The term "racemic" refers to a mixture of equal parts of enantiomers and which is optically inactive.

The term "resolution" refers to the separation or concentration or depletion of one of the two enantiomeric forms of a molecule. The phrase "enantiomeric excess" refers to a mixture wherein one enantiomer is present is a greater concentration than its mirror image molecule.

The phrase "having the formula" or "having the structure" is not intended to be limiting and is used in the same way that the term "comprising" is commonly used.

The term "analog" means a compound in which one or more individual atoms have been replaced, either with a different atom, or with a different functional group and where replacement of the atom does not substantially eliminate or reduce the compounds ability to act as a PTPase inhibitor.

In another aspect of the present invention, the PTPase inhibitor can be a benzo-1,4-quinone have any one of the following formulas:

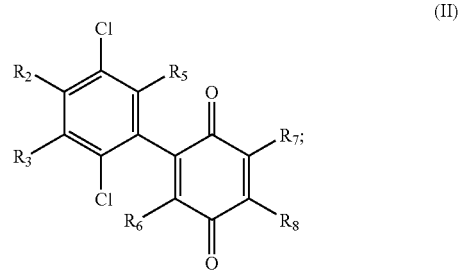

(II)

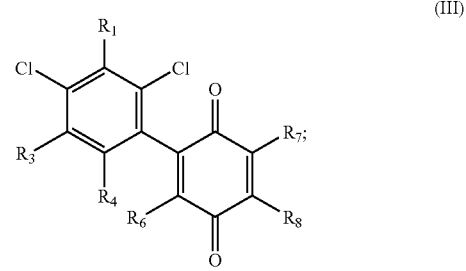

(III)

-continued

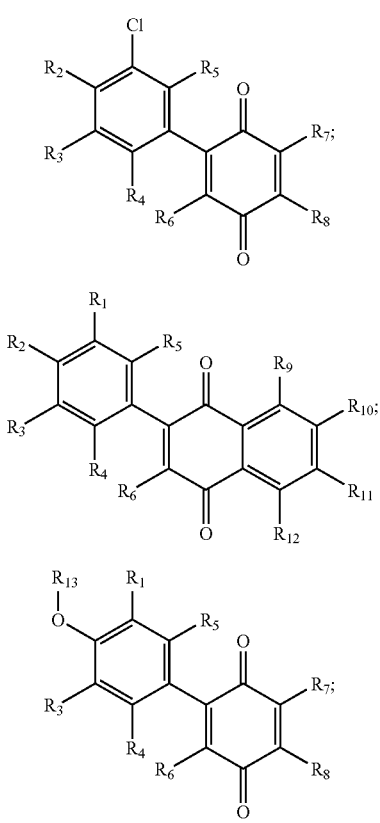

where $R_9$, $R_{10}$, $R_{11}$, $R_{12}$, and $R_{13}$ each independently represent substituents selected from the group consisting of hydrogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, $C_2$-$C_{24}$ alkylcarbonyl (—CO-alkyl), $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano(—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino, alkylimino, arylimino, nitro (—NO$_2$), nitroso (—NO), sulfo (—SO$_2$—OH), sulfonato (—SO$_2$—O$^-$), $C_1$-$C_{24}$ alkylsulfanyl (—S-alkyl), arylsulfanyl, $C_1$-$C_{24}$ alkylsulfinyl (—(SO)-alkyl), $C_5$-$C_{20}$-arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), phosphino (—PH$_2$), and combinations thereof; or a pharmaceutically acceptable salt thereof.

In still another aspect of the present invention, the benzo-1,4-quinone can have any one of following formulas:

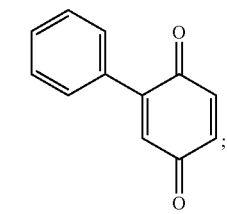
(Ia)

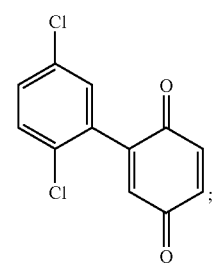
(IIa)

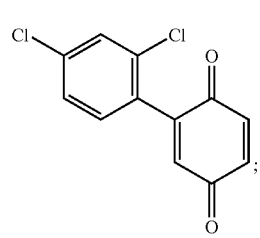
(IIIa)

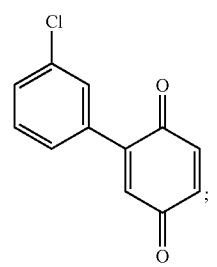
(IVa)

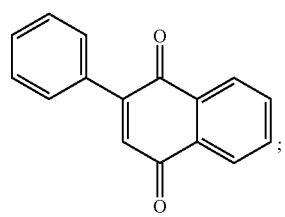
(Va)

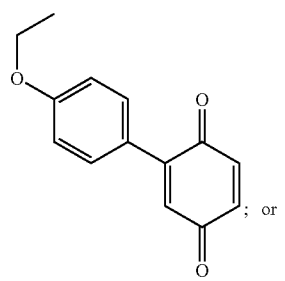
(VIa)

; or

-continued

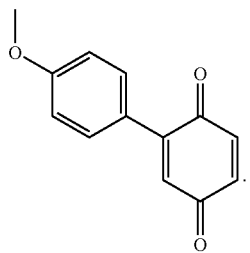

(VIb)

In another aspect of the invention, the phenyl isothiazolone or analog thereof can comprise the formula (VII):

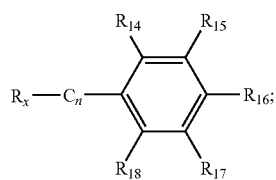

(VII)

where Rx is a isothiazolone or analog thereof comprising a heterocyclic five membered ring containing at least one nitrogen atom and sulfur atom in the ring;

n is 0 or 1;

$R_{14}$, $R_{15}$, $R_{16}$, $R_{17}$, and $R_{18}$ each independently represent substituents selected from the group consisting of hydrogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, $C_2$-$C_{24}$ alkylcarbonyl (—CO-alkyl), $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano(—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino, alkylimino, arylimino, nitro (—NO$_2$), nitroso (—NO), sulfo (—SO$_2$—OH), sulfonato (—SO$_2$—O$^-$), $C_1$-$C_{24}$ alkylsulfanyl (—S-alkyl), arylsulfanyl, $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), phosphino (—PH$_2$), and combinations thereof; or a pharmaceutically acceptable salt thereof.

In a further aspect, the phenyl isothiazolone or analog thereof can comprise at least one of the following formulas:

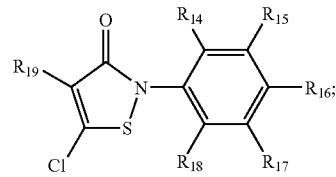

(VIII)

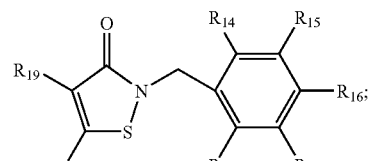

(IX)

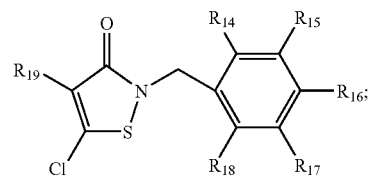

(X)

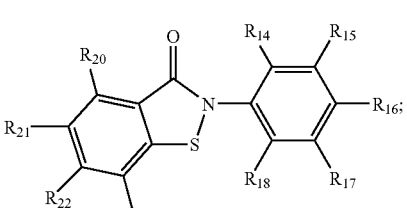

(XI)

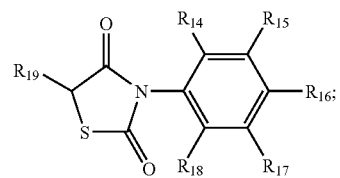

where $R_{14}$, $R_{15}$, $R_{16}$, $R_{17}$, $R_{18}$, $R_{19}$, $R_{20}$, $R_{21}$, $R_{22}$ and $R_{23}$ each independently represent substituents selected from the group consisting of hydrogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, $C_2$-$C_{24}$ alkylcarbonyl (—CO-alkyl), $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano (—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino, alkylimino, arylimino, nitro (—NO$_2$), nitroso (—NO), sulfo (—SO$_2$—OH), sulfonato (—SO$_2$—O$^-$), $C_1$-$C_{24}$ alkylsulfanyl (—S-alkyl), arylsulfanyl, $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), phosphino (—PH$_2$), and combinations thereof; or a pharmaceutically acceptable salt thereof.

In a still further aspect, the phenyl isothiazolone or analog thereof can comprise at least one of the following formulas:

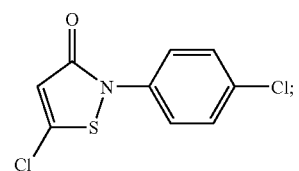
(VIIIa)

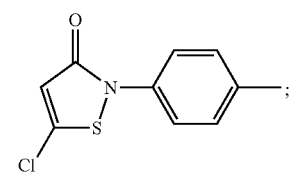<br>
(VIIIb)

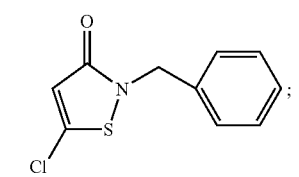<br>
(IXa)

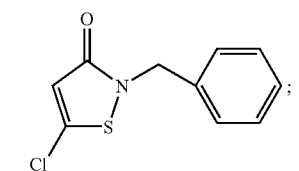<br>
(IXa)

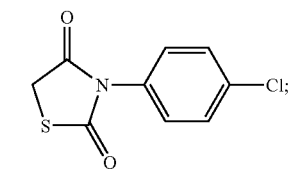<br>
(XIa)

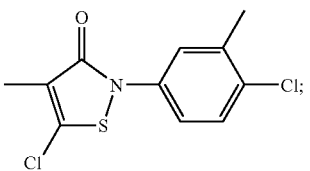<br>
(VIIIc)

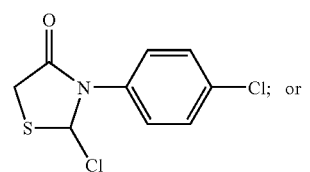<br>
(XIIa)

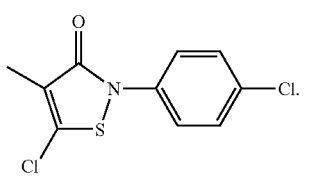<br>
(VIIId)

In another aspect of the invention, PTPase inhibitor can comprise at least one compound having a formula selected from the group consisting of:

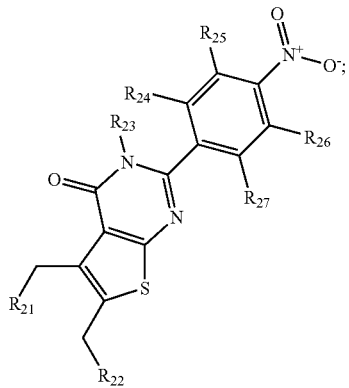
(XIII)

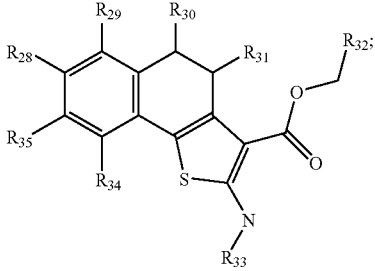
(XIV)

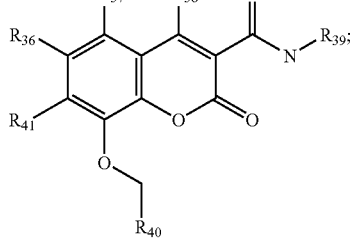
(XV)

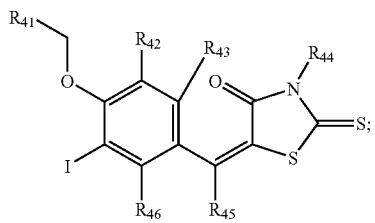
(XVI)

where $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, $R_{36}$, $R_{37}$, $R_{38}$, $R_{39}$, $R_{40}$, $R_{41}$, $R_{42}$, $R_{43}$, $R_{44}$, $R_{45}$ and $R_{46}$ each independently represent substituents selected from the group consisting of hydrogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, $C_2$-$C_{24}$ alkylcarbonyl (—CO-alkyl), $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO⁻), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano (—CN), isocyano (—N⁺C⁻), cyanato (—O—CN), isocyanato (—O—N⁺=C⁻), isothiocyanato (—S—CN), azido (—N=N⁺=N⁻), formyl (—(CO)—H), thioformyl (—(CS)—H), amino (—NH$_2$), mono- and di-(C$_1$-C$_{24}$ alkyl)-substituted amino, mono- and di-(C$_5$-C$_{20}$ aryl)-substituted amino, C$_2$-C$_{24}$ alkylamido (—NH—(CO)-alkyl), C$_6$-C$_{20}$ arylamido (—NH—(CO)-aryl), imino, alkylimino, arylimino, nitro (—NO$_2$), nitroso (—NO), sulfo (—SO$_2$—OH), sulfonato (—SO$_2$—O⁻), C$_1$-C$_{24}$ alkylsulfanyl (—S-alkyl), arylsulfanyl, C$_1$-C$_{24}$ alkylsulfinyl (—(SO)-alkyl), C$_5$-C$_{20}$ arylsulfinyl (—(SO)-aryl), C$_1$-C$_{24}$ alkylsulfonyl (—SO$_2$-alkyl), C$_5$-C$_{20}$ arylsulfonyl (—SO$_2$-aryl), phosphono (—P(O)(OH)$_2$), phosphonato (—P(O)(O⁻)$_2$), phosphinato (—P(O)(O⁻)), phospho (—PO$_2$), phosphino (—PH$_2$), and combinations thereof; or a pharmaceutically acceptable salt thereof.

In a still further aspect of the invention, PTPase inhibitor can comprise at least one compound having a formula selected from the group consisting of:

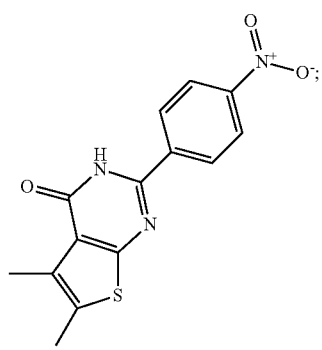

(XIIIa)

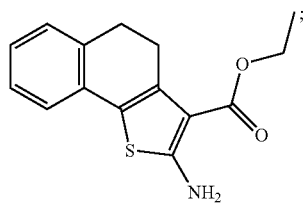

(XIVa)

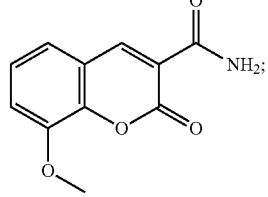

(XVa)

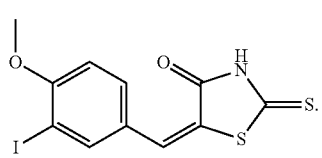

(XVIa)

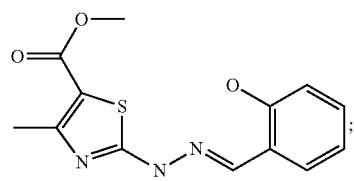

(XVII)

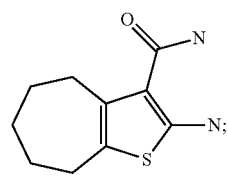

(XVIII)

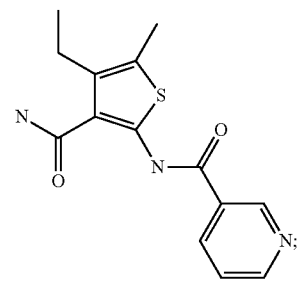

(XIX)

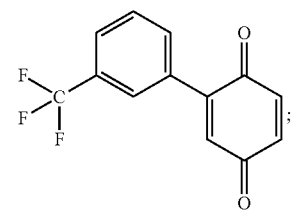

(XX)

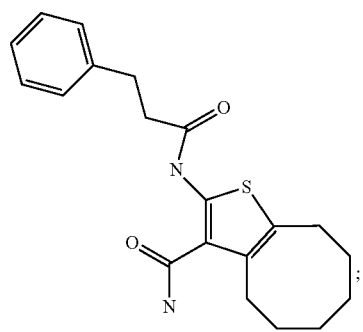

(XXI)

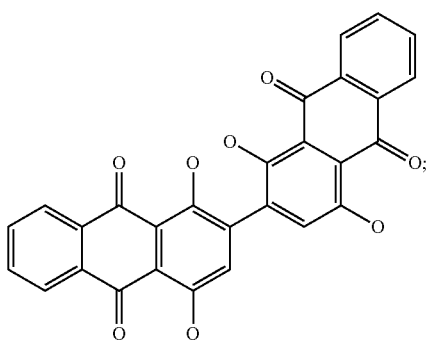

(XXII)

In yet another aspect of the invention, PTPase inhibitor can comprise at least one compound having a formula selected from the group consisting of:

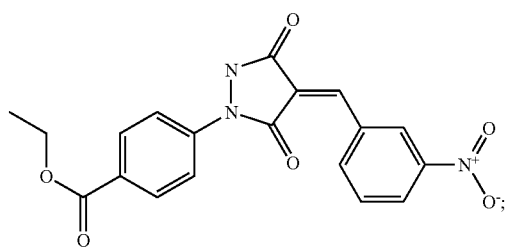
(XXIII)
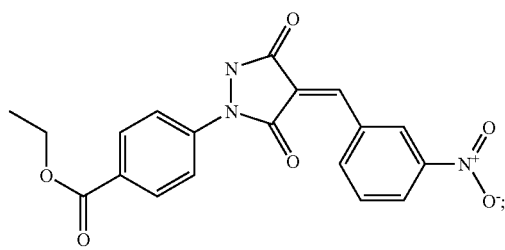
(XXIII)
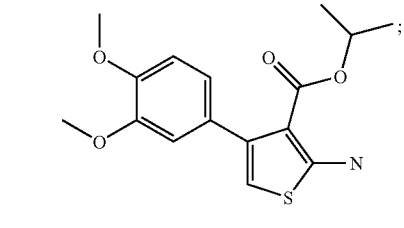
(XXV)
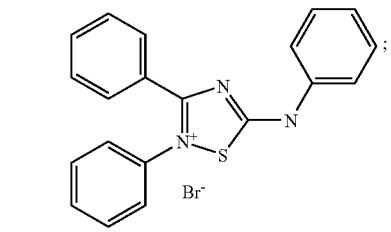
(XXVI)
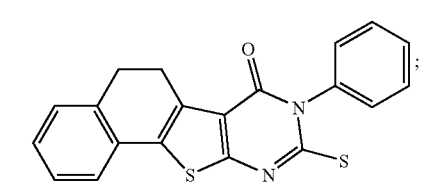
(XXVII)
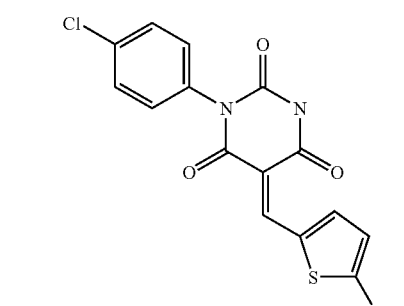
(XXIX)
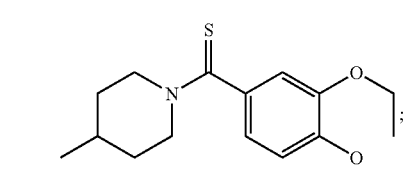
(XXX)
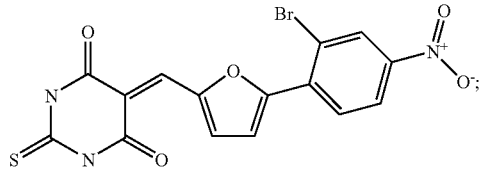
(XXXI)
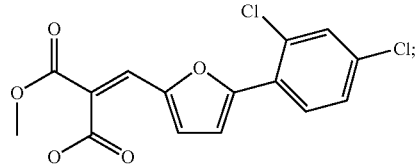
(XXXII)
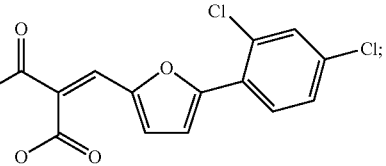
(XXXIII)
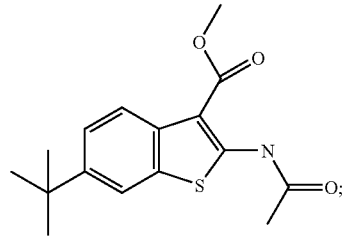
(XXXIII)
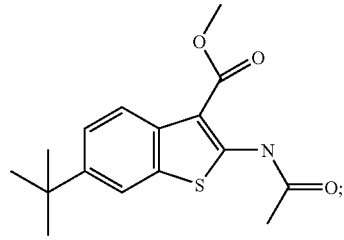
(XXXIII)
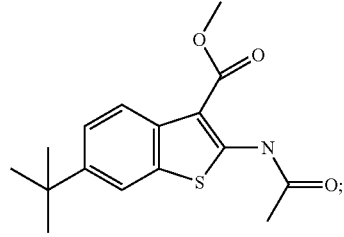
(XXXIII)
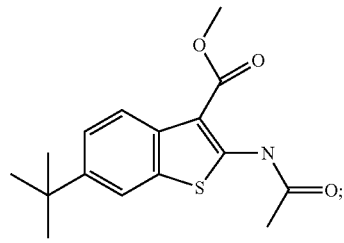
(XXXIII)

-continued

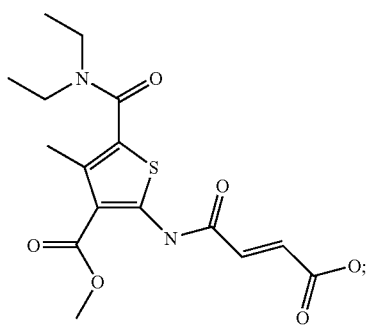

(XXXVII)

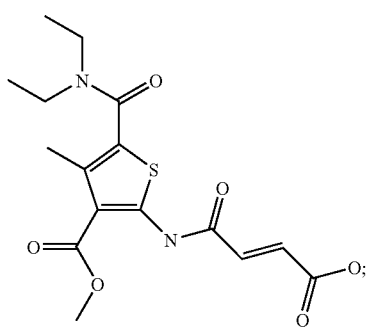

(XXXVIII)

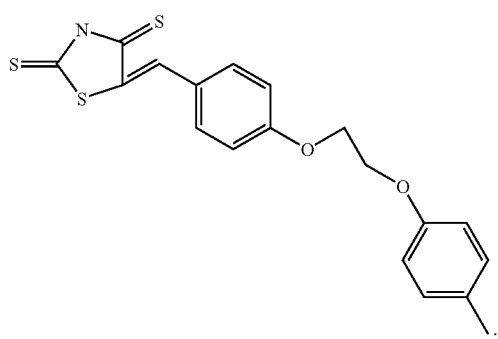

(XXXIX)

The PTPase inhibitors of the present invention can be provided in the form of pharmaceutical compositions. The pharmaceutical compositions can be administered to any animal that can experience the beneficial effects of the PTPase inhibitors of the present invention. Foremost among such animals are humans, although the present invention is not intended to be so limited.

The pharmaceutical compositions of the present invention can be administered by any means that achieve their intended purpose. For example, administration can be by parenteral, subcutaneous, intravenous, intraarticular, intrathecal, intramuscular, intraperitoneal, or intradermal injections, or by transdermal, buccal, oromucosal, ocular routes or via inhalation. Alternatively or concurrently, administration can be by the oral route. Particularly preferred is oral administration. The dosage administered will be dependent upon the age, health, and weight of the patient, kind of concurrent treatment, if any, frequency of treatment, and the nature of the effect desired.

In addition to the pharmacologically active compounds, the pharmaceutical preparations of the PTPase inhibitors can contain suitable pharmaceutically acceptable carriers comprising excipients and auxiliaries that facilitate processing of the active agents into preparations that can be used pharmaceutically. The pharmaceutical preparations of the present invention are manufactured in a manner that is, itself, known, for example, by means of conventional mixing, granulating, dragee-making, dissolving, or lyophilizing processes. Thus, pharmaceutical preparations for oral use can be obtained by combining the active agents with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings, that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as acetylcellulose phthalate or hydroxypropylmethylcellulose phthalate, are used. Slow-release and prolonged-release formulations may be used with particular excipients such as methacrylic acid-ethylacrylate copolymers, methacrylic acid-ethyl acrylate copolymers, methacrylic acid-methyl methacrylate copolymers and methacrylic acid-methyl methylacrylate copolymers. Dye stuffs or pigments can be added to the tablets or dragee coatings, for example, for identification or in order to characterize combinations of active compound doses.

Other pharmaceutical preparations that can be used orally include push-fit capsules made of gelatin, as well as soft, sealed capsules made of gelatin and a plasticizer such as glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids such as fatty oils or liquid paraffin. In addition, stabilizers may be added.

Examples of formulations for parenteral administration include aqueous solutions of the active compounds in water-soluble form, for example, water-soluble salts and alkaline solutions. Especially preferred salts are maleate, fumarate, succinate, S,S tartrate, or R,R tartrate. In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example sodium carboxymethyl cellulose, sorbitol, and/or dextran. Optionally, the suspension may also contain stabilizers.

In certain embodiments, PTPase inhibitors of the invention can be delivered to cancer cells by site-specific means. Cell-type-specific delivery can be provided by conjugating a therapeutic agent to a targeting molecule, for example, one that selectively binds to the affected cells. Methods for targeting include conjugates, such as those described in U.S. Pat. No. 5,391,723, which is herein incorporated by reference in its entirety. Targeting vehicles, such as liposomes, can be used to deliver a compound, for example, by encapsulating the compound in a liposome containing a cell-specific targeting molecule. Methods for targeted delivery of compounds to particular cell types are well-known to those skilled in the art.

In a further aspect of the invention, the pharmaceutical composition comprising the at least one PTPase inhibitor in accordance with the present invention can be used to treat a variety of diseases. For example, a therapeutically effective amount of a PTPase inhibitor can be used to treat a disease responsive to cytokine treatment, a disease associated with an immune deficiency, and/or cancer.

In another aspect of the present invention, administering a therapeutically effective amount of the PTPase inhibitor of the present invention to a patient having a disease responsive to cytokine treatment may modulate or inhibit SHP-1 and/or MKP-1. By effectively modulating or inhibiting SHP-1 or MKP-1, pLck may be sufficiently increased to affect a change (i.e., activate) in at least one immune cell. Where the effected immune cell comprises a T cell, for example, the T cell may become sufficiently activated so as to produce at least one cytokine, such as interferon gamma (IFNγ). The activated T cell(s) may then produce a sufficient amount of IFNγ to effectively treat the particular disease. Examples of diseases responsive to cytokine treatment include, without limitation, allergic diseases such as asthma, renal cell carcinoma, melanomas, and infectious diseases caused by viral infections (e.g., Hepatitis C).

In another aspect of the present invention, administering a therapeutically effective amount of the PTPase inhibitor to a patient having an immune deficiency may modulate or inhibit SHP-1 and/or MKP-1. An immune deficiency is a disease or disorder in which part of a patient's immune system is missing or does not function properly (e.g., HIV/AIDS). By effectively modulating or inhibiting SHP-1 and/or MKP-1, pLck may be sufficiently increased to affect a change (i.e., activate) in at least one immune cell. Where the immune cell comprises a T cell, the T cell may become sufficiently activated so as to produce at least one cytokine, such as IFNγ. Production of cytokines and/or growth factors is critical for proper hematopoietic cell development. By inhibiting SHP-1 and, in turn, stimulating cytokine production, hematopoietic cells may be prompted to expand and develop into the cell types depleted as a result of the immune deficiency.

In another aspect of the present invention, administering a therapeutically effective amount of the PTPase inhibitor of the present invention to a patient having cancer may effectively modulate or inhibit SHP-2. By modulating or inhibiting SHP-2 and/or MKP-1, pErk1/2 may be sufficiently reduced so as to affect a reduction in cellular proliferation. Consequently, uncontrolled cell growth and proliferation (i.e., cancer) may be reduced or inhibited. The cancer may be, but is not limited to, lymphoma, multiple myeloma, leukemia, melanoma, prostate cancer, breast cancer, renal cancer, and bladder cancer. This aspect of the present invention may also be used to treat a patient with multiple cancers.

In a further aspect of the invention, the PTPase inhibitors of the present invention can be used in combination and adjunctive therapies for treating proliferative disorders. The phrase "combination therapy" embraces the administration of the PTPase inhibitors, and a therapeutic agent as part of a specific treatment regimen intended to provide a beneficial effect from the co-action of these therapeutic agents. Administration of these therapeutic agents in combination typically is carried out over a defined time period (usually minutes, hours, days or weeks depending upon the combination selected).

"Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues.

The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" also can embrace the administration of the therapeutic agents as described above in further combination with other biologically active ingredients (such as, but not limited to, a second and different therapeutic agent) and non-drug therapies (such as, but not limited to, surgery or radiation treatment). Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

The phrase "adjunctive therapy" encompasses treatment of a subject with agents that reduce or avoid side effects associated with the combination therapy of the present invention, including, but not limited to, those agents, for example, that reduce the toxic effect of anticancer drugs, e.g., bone resorption inhibitors, cardioprotective agents; prevent or reduce the incidence of nausea and vomiting associated with chemotherapy, radiotherapy or operation; or reduce the incidence of infection associated with the administration of myelosuppressive anticancer drugs.

The mammalian disease treated by the combination therapy can include proliferative diseases, such as neoplastic disorders (e.g., leukemia) and autoimmune dysfunctions as well as viral and microbial infections. Besides being useful for human treatment, the combination therapy is also useful for veterinary treatment of companion animals, exotic and farm animals, including rodents, horses, dogs, and cats.

In another aspect of the invention, the therapeutic agents administered in combination therapy with the PTPase inhibitor can comprise at least one anti-proliferative agent selected from the group consisting of a chemotherapeutic agent, an antimetabolite, an antitumorgenic agent, an antimitotic agent, an antiviral agent, an antineoplastic agent, an immunotherapeutic agent, and a radiotherapeutic agent.

The phrase "anti-proliferative agent" can include agents that exert antineoplastic, chemotherapeutic, antiviral, antimitotic, antitumorgenic, and/or immunotherapeutic effects, e.g., prevent the development, maturation, or spread of neoplastic cells, directly on the tumor cell, e.g., by cytostatic or cytocidal effects, and not indirectly through mechanisms such as biological response modification. There are large numbers of anti-proliferative agent agents available in commercial use, in clinical evaluation and in pre-clinical development, which could be included in the present invention by combination drug chemotherapy. For convenience of discussion, anti-proliferative agents are classified into the following classes, subtypes and species: ACE inhibitors, alkylating agents, angiogenesis inhibitors, angiostatin, anthracyclines/DNA intercalators, anti-cancer antibiotics or antibiotic-type agents, antimetabolites, antimetastatic compounds, asparaginases, bisphosphonates, cGMP phosphodiesterase inhibitors, calcium carbonate, cyclooxygenase-2 inhibitors, DHA derivatives, DNA topoisomerase, endostatin, epipodophylotoxins, genistein, hormonal anticancer agents, hydrophilic bile acids (URSO), immunomodulators or immunological agents, integrin antagonists, interferon antagonists or agents, MMP inhibitors, miscellaneous antineoplastic agents, monoclonal antibodies, nitrosoureas, NSAIDs, ornithine decarboxylase inhibitors, pBATTs, radio/chemo sensitizers/protectors, retinoids, selective inhibitors of proliferation and migration of endotheliai cells, selenium, stromelysin inhibitors, taxanes, vaccines, and vinca alkaloids.

The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category.

A first family of anti-proliferative agents, which may be used in combination therapy PTPase inhibitors consists of antimetabolite-type anti-proliferative agents. Antimetabolites are typically reversible or irreversible enzyme inhibitors, or compounds that otherwise interfere with the replication, translation or transcription of nucleic acids. Examples of antimetabolite antineoplastic agents that may be used in the present invention include, but are not limited to acanthifolic acid, aminothiadiazole, anastrozole, bicalutamide, brequinar sodium, capecitabine, carmofur, Ciba-Geigy CGP-30694, cladribine, cyclopentyl cytosine, cytarabine phosphate stearate, cytarabine conjugates, cytarabine ocfosfate, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, finasteride, floxuridine, fludarabine phosphate, N-(2'-furanidyl)-5-fluorouracil, Daiichi Seiyaku FO-152, fluorouracil (5-FU), 5-FU-fibrinogen, isopropyl pyrrolizine, Lilly LY-188011, Lilly LY-264618, methobenzaprim, methotrexate, Wellcome MZPES, nafarelin, norspermidine, nolvadex, NCI NSC-127716, NCI NSC-264880, NCI NSC-39661, NCI NSC-612567, Warner-Lambert PALA, pentostatin, piritrexim, plicamycin, Asahi Chemical PL-AC, stearate; Takeda TAC-788, thioguanine, tiazofurin, Erbamont TIF, trimetrexate, tyrosine kinase inhibitors, tyrosine protein kinase inhibitors, Taiho UFT, toremifene, and uricytin, all of which are disclosed in U.S. Pat. No. 6,916,800, which is herein incorporated by reference in its entirety.

A second family of anti-proliferative agents, which may be used in combination therapy with the PTPase inhibitors of the present invention consists of alkylating-type anti-proliferative agents. The alkylating agents are believed to act by alkylating and cross-linking guanine and possibly other bases in DNA, arresting cell division. Typical alkylating agents include nitrogen mustards, ethyleneimine compounds, alkyl sulfates, cisplatin, and various nitrosoureas. A disadvantage with these compounds is that they not only attack malignant cells, but also other cells which are naturally dividing, such as those of bone marrow, skin, gastro-intestinal mucosa, and fetal tissue. Examples of alkylating-type anti-proliferative agents that may be used in the present invention include, but are not limited to, Shionogi 254-S, aldo-phosphamide analogues, altretamine, anaxirone, Boehringer Mannheim BBR-2207, bestrabucil, budotitane, Wakunaga CA-102, carboplatin, carmustine (BiCNU), Chinoin-139, Chinoin-153, chlorambucil, cisplatin, cyclophosphamide, American Cyanamid CL-286558, Sanofi CY-233, cyplatate, dacarbazine, Degussa D-19-384, Sumimoto DACHP(Myr)$_2$, diphenylspiromustine, diplatinum cytostatic, Erba distamycin derivatives, Chugai DWA-2114R, ITI E09, elmustine, Erbamont FCE-24517, estramustine phosphate sodium, etoposide phosphate, fotemustine, Unimed G-6-M, Chinoin GYKI-17230, hepsul-fam, ifosfamide, iproplatin, lomustine, mafosfamide, mitolactol, mycophenolate, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, thiotepa, Yakult Honsha SN-22, spiromus-tine, Tanabe Seiyaku TA-077, tauromustine, temozolomide, teroxirone, tetraplatin and trimelamol.

A third family of anti-proliferative agents that may be used in combination therapy with the PTPase inhibitors of the present invention consists of antibiotic-type anti-proliferative agents. Examples of antibiotic-type anti-proliferative agents that may be used in the present invention include, but are not limited to Taiho 4181-A, aclarubicin, actinomycin D, actinoplanone, Erbamont ADR-456, aeroplysinin derivative, Ajinomoto AN-201-11, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of anti-proliferative agents that may be used in combination therapy with the PTPase inhibitors of the present invention consists of synthetic nucleosides. Several synthetic nucleosides have been identified that exhibit anti-cancer activity. A well known nucleoside derivative with strong anticancer activity is 5-fluorouracil (5-FU). 5-Fluorouracil has been used clinically in the treatment of malignant tumors, including, for example, carcinomas, sarcomas, skin cancer, cancer of the digestive organs, and breast cancer.

5-Fluorouracil, however, causes serious adverse reactions such as nausea, alopecia, diarrhea, stomatitis, leukocytic thrombocytopenia, anorexia, pigmentation, and edema. Derivatives of 5-fluorouracil with anti-cancer activity have been described in U.S. Pat. No. 4,336,381, which is herein incorporated by reference in its entirety.

A fifth family of anti-proliferative agents that may be used in combination therapy with the PTPase inhibitors of the present invention consists of hormonal agents. Examples of hormonal-type anti-proliferative agents that may be used in the present invention include, but are not limited to Abarelix; Abbott A-84861; Abiraterone acetate; Aminoglutethimide; anastrozole; Asta Medica AN-207; Antide; Chugai AG-041R; Avorelin; aseranox; Sensus B2036-PEG; Bicalutamide; buserelin; BTG CB-7598; BTG CB-7630; Casodex; cetrolix; clastroban; clodronate disodium; Cosudex; Rotta Research CR-1505; cytadren; crinone; deslorelin; droloxifene; dutasteride; Elimina; Laval University EM-800; Laval University EM-652; epitiostanol; episteride; Mediolanum EP-23904; EntreMed 2-ME; exemestane; fadrozole; finasteride; flutamide; formestane; Pharmacia & Upjohn FCE-24304; ganirelix; goserelin; Shire gonadorelin agonist; Glaxo Wellcome GW-5638; Hoechst Marion Roussel Hoe-766; NCI hCG; idoxifene; isocordoin; Zeneca ICI-182780; Zeneca ICI-118630; Tulane University J015X; Schering Ag J96; ketanserin; lanreotide; Milkhaus LDI-200; letrozol; leuprolide; leuprorelin; liarozole; lisuride hydrogen maleate; loxiglumide; mepitiostane; Leuprorelin; Ligand Pharmaceuticals LG-1127; LG-1447; LG-2293; LG-2527; LG-2716; Bone Care International LR-103; Lilly LY-326315; Lilly LY-353381-HCl; Lilly LY-326391; Lilly LY-353381; Lilly LY-357489; miproxifene phosphate; Orion Pharma MPV-2213ad; Tulane University MZ-4-71; nafarelin; nilutamide; Snow Brand NKS01; octreotide; Azko Nobel ORG-31710; Azko Nobel ORG-31806; orimeten; orimetene; orimetine; ormeloxifene; osaterone; Smithkline Beecham SKB-105657; Tokyo University OSW-1; Peptech PTL-03001; Pharmacia & Upjohn PNU-156765; quinagolide; ramorelix; Raloxifene; statin; sandostatin LAR; Shionogi S-10364; Novartis SMT-487; somavert; somatostatin; tamoxifen; tamoxifen methiodide; teverelix; toremifene; triptorelin; TT-232; vapreotide; vorozole; Yamanouchi YM-116; Yamanouchi YM-511; Yamanouchi YM-55208; Yamanouchi YM-53789; Schering AG ZK-1911703; Schering AG ZK-230211; and Zeneca ZD-182780.

A sixth family of anti-proliferative agents that may be used in combination therapy with the PTPase inhibitors of the present invention consists of a miscellaneous family of antineoplastic agents including, but not limited to alpha-carotene, alpha-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluoron, benzotript, Ipsen-Beaufour BIM-23015, bisantrene, Bristo-Myers BMY-40481, Vestar boron-10, bromofosfamide, Wellcome BW-502, Wellcome BW-773, calcium carbonate, Calcet, Calci-Chew, Calci-Mix, Roxane calcium carbonate tablets, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Cell Pathways CP-461, Yakult Honsha CPT-11, crisnatol, curaderm, cytochalasin B, cytarabine, cytocytin, Merz D-609, DABIS maleate, dacarbazine, datelliptinium, DFMO, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel, Encore Pharmaceuticals E7869, elliprabin, elliptinium acetate, Tsumura EPMTC, ergotamine, etoposide, etretinate, Eulexin®, Cell Pathways Exisulind® (sulindac sulphone or CP-246), fenretinide, Merck Research Labs Finasteride, Florical, Fujisawa FR-57704, gallium nitrate, gemcitabine, genkwadaphnin, Gerimed, Chugai GLA-43, Glaxo GR-63178, grifolan NMF-5N, hexadecylphosphocholine, Green Cross HO-221, homoharringtonine, hydroxyurea, BTG ICRF-187, ilmofosine, irinotecan, isoglutamine, isotretinoin, Otsuka JI-36, Ramot K-477, ketoconazole, Otsuak K-76COONa, Kureha Chemical K-AM, MECT Corp KI-8110, American Cyanamid L-623, leucovorin, levamisole, leukoregulin, lonidamine, Lundbeck LU-23-112, Lilly LY-186641, Materna, NCI (US) MAP, marycin, Merrel Dow MDL-27048, Medco MEDR-340, megestrol, merbarone, merocyanine derivatives, methylanilinoacridine, Molecular Genetics MGI-136, minactivin, mitonafide, mitoquidone, Monocal, mopidamol, motretinide, Zenyaku Kogyo MST-16, Mylanta, N-(retinoyl)amino acids, Nilandron; Nisshin Flour Milling N-021, N-acylated-dehydroalanines, nafazatrom, Taisho NCU-190, Nephro-Calci tablets, nocodazole derivative, Normosang, NCI NSC-145813, NCI NSC-361456, NCI NSC-604782, NCI NSC-95580, octreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, retinoids, Encore Pharmaceuticals R-flurbiprofen, Sandostatin; Sapporo Breweries RBS, restrictin-P, retelliptine, retinoic acid, Rhone-Poulenc RP-49532, Rhone-Poulenc RP-56976, Scherring-Plough SC-57050, Scherring-Plough SC-57068, seienium(selenite and selenomethionine), SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, Sugen SU-01, Sugen SU-5416, Sugen SU-6668, sulindac, sulindac sulfone; superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides, Yamanouchi YM-534, Zileuton, ursodeoxycholic acid, and Zanosar.

In a specific embodiment, the methods of the invention can also encompass administration of a PTPase inhibitor of the invention in combination with the administration of one or more prophylactic/therapeutic agents that are inhibitors of kinases such as, but not limited to, ABL, ACK, AFK, AKT (e.g., AKT-1, AKT-2, and AKT-3), ALK, AMP-PK, ATM, Auroral, Aurora2, bARKI, bArk2, BLK, BMX, BTK, CAK, CaM kinase, CDC2, CDK, CK, COT, CTD, DNA-PK, EGF-R, ErbB-1, ErbB-2, ErbB-3, ErbB-4, ERK (e.g., ERK1, ERK2, ERK3, ERK4, ERK5, ERK6, ERK7), ERT-PK, FAK, FGR (e.g., FGF1R, FGF2R), FLT (e.g., FLT-1, FLT-2, FLT-3, FLT-4), FRK, FYN, GSK (e.g., GSK1, GSK2, GSK3-alpha, GSK3-beta, GSK4, GSK5), G-protein coupled receptor kinases (GRKs), HCK, HER2, HKII, JAK (e.g., JAK1, JAK2, JAK3, JAK4), JNK (e.g., JNK1, JNK2, JNK3), KDR, KIT, IGF-1 receptor, IKK-1, IKK-2, INSR (insulin receptor), IRAK1, IRAK2, IRK, ITK, LCK, LOK, LYN, MAPK, MAP-KAPK-1, MAPKAPK-2, MEK, MET, MFPK, MHCK, MLCK, MLK3, NEU, NIK, PDGF receptor alpha, PDGF receptor beta, PHK, PI-3 kinase, PKA, PKB, PKC, PKG, PRK1, PYK2, p38 kinases, p135tyk2, p34cdc2, p42cdc2, p42mapk, p44 mpk, RAF, RET, RIP, RIP-2, RK, RON, RS kinase, SRC, SYK, S6K, TAK1, TEC, TIE1, TIE2, TRKA, TXK, TYK2, UL13, VEGFR1, VEGFR2, YES, YRK, ZAP-70, and all subtypes of these kinases (see e.g., Hardie and Hanks (1995) The Protein Kinase Facts Book, I and II, Academic Press, San Diego, Calif.), which herein incorporarated by reference in its entirety.

The PTPase inhibitors in accordance with the present invention can allow the combination therapeutic agents and therapies of the present invention to be administered at a low dose, that is, at a dose lower than has been conventionally used in clinical situations.

A benefit of lowering the dose of the combination therapeutic agents and therapies of the present invention administered to a mammal includes a decrease in the incidence of adverse effects associated with higher dosages. For example, by the lowering the dosage of a chemotherapeutic agent such as 5-FU, a reduction in the frequency and the severity of nausea and vomiting will result when compared to that observed at higher dosages. Similar benefits are contemplated for the compounds, compositions, agents and therapies in combination with the inhibitors of the present invention.

By lowering the incidence of adverse effects, an improvement in the quality of life of a patient undergoing treatment for cancer is contemplated. Further benefits of lowering the incidence of adverse effects include an improvement in patient compliance, a reduction in the number of hospitalizations needed for the treatment of adverse effects, and a reduction in the administration of analgesic agents needed to treat pain associated with the adverse effects.

Alternatively, the methods and combination of the present invention can also maximize the therapeutic effect at higher doses.

When administered as a combination, the PTPase inhibitors can be formulated as separate compositions which are given at the same time or different times, or the therapeutic agents can be given as a single composition.

The following examples are for the purpose of illustration only and are not intended to limit the scope of the claims, which are appended hereto.

EXAMPLES

Example 1

SHP-1 and SHP-2 as Anti-Cancer Target Molecules

SHP-1 is a key negative regulator in anti-tumor immune cells, including T cells, NK cells, and macrophage cells. T cells with genetic SHP-1 deficiency mount stronger immune responses to weak antigens. Similarly, NK cells and macrophage cells become hyperactive in the absence protein tyrosine phosphatases (PTPases). Hematopoietic cells in general are hyper-responsive to cytokines and hematopoietic growth factors.

The key SHP-1 substrate in T cell activation is the Lck kinase (FIG. 1). Lck becomes phosphorylated (pLck) and activated following antigen binding to TCR. Its dephosphorylation (tyrosine 394) by SHP-1 inactivates the kinase and terminates TCR signaling. Thus, targeting SHP-1 by an inhibitor will increase pLck and activate T cells.

SHP-2 is a transducer of mitogenic signaling. It is activated due to point mutations in human malignancies and plays a causal role in oncogenesis. It functions down stream of kinase receptors to induce phosphorylated Erk1/2 (pErk1/2). Accordingly, inhibition of SHP-2 will reduce cell proliferation in association with a reduction of pErk1/2 (FIG. 1).

Sodium Stibogluconate (SSG) as the First SHPs-Targeted Anti-Cancer Agent

Our studies have provided evidence that: (1) SSG inhibits recombinant and intracellular SHP-1 and SHP-2 at clinically achievable levels (10 µg/ml); (2) SSG modulates cell responses to cytokines/hematopoietic growth factors in consistence with targeting SHPs; (3) SSG had anti-tumor activity alone and, more effectively, with IFNα2 or IL-2 in mouse models; (4) SSG anti-tumor action is mediated both via activating immune cells (IFNγ+ T cells) and direct growth inhibition of tumor cells, consistent with targeting SHPs. However, its structural complexity and the difficulties associated with administration (daily I.V.) limit its application and prompted us to develop refined small chemical inhibitors for the SHPs.

Novel SHPs Inhibitor Leads from High Throughput Screening of a Chemical Library

To identify novel and more potent SHP-1 inhibitory lead compounds, a library of 34,000 drug-like small chemicals was screened by a rapid in vitro SHP-1 PTPase assay. Focusing on key activities essential for pre-clinical efficacy and tolerance of SHP-1-targeted anti-cancer agents, identified leads were further selected based on their capacity to inhibit intracellular SHP-1 in T cells, to induce primary IFNγ+ T cells and to act against malignant tumors in mouse models. This strategy has led to the identification of L5 as a novel SHP-1 inhibitor more potent than SSG and had significant activity against malignant B16 melanoma tumors in mice when delivered orally at a tolerated dose. Our results provide further evidence supporting targeting PTPases as an anti-cancer strategy and designate L5 as a promising lead compound for the development of SHP-1-targeted anti-cancer therapeutics.

Materials and Methods

Cells, Cell Culture and Reagents

Recombinant protein of SHP-1 PTPase catalytic domain was described and stored in Tris buffer (25 mM Tris, pH7.5, 1 mM EDTA, 2 µM 2-ME, 25% glycerol) at −80° C. Fluorescence substrate DIFMUP (6,8-difluoro-4 methylumbelliferyl phosphate) was purchased (Molecular Probes). SSG was reported previously (21-23) and stored at 4° C. in darkness prior to use. Human and mouse IFNγ ELISPOT Kit (R & D System), CD4+ Cell Intracellular IFNγ Detection Kit (BD Bioscience) and CD8+ Cell Intracellular IFNγ Detection Kit (BD Bioscience) were purchased from commercial sources. Human Jurkat T cell line (26) and murine B16 melanoma cell line (ATCC) were maintained in DMSO culture medium supplemented with 10% fetal calf serum (FCS). Antibodies against pLck-pY394 (Cell Signaling), pLck-pY505 (Cell Signaling), pZap70 (pY319, BD Biosciences), pSlp76 (pY128, BD Biosciences) and pLat (pY226, BD Biosciences) were purchased from commercial sources.

Screening of Chemical Library by In Vitro PTPase Assay

A rapid SHP-1 PTPase assay was developed for screening the compounds in a commercial library of 34,000 drug-like small chemicals (Chembridge, Mass.). Briefly, compounds of the library (1 µg/well in 0.21 DMSO) were placed in 96-well plates (Falcon, 353072) and mixed with recombinant SHP-1 protein (0.1 µg/well) in 90l of HEPES buffer (50 mM HEPS, pH 7.5, 150 mM NaCl, 1 mM EDTA, 0.2 mM DTT and 0.1 mg/ml BSA). The plates were incubated at room temperature for 10 minutes prior to the addition of fluorescence substrate DIFMUP (40 µM stock in HEPES buffer, 10 µl/well) to initiate PTPase reaction. Upon completion of PTPase reaction at room temperature for 1 hr in darkness, fluorescence signal of individual wells were recorded using a Vector$^2$ Multilabel Counter (Vector, CA). They were compared to that of control SHP-1 PTPase reaction (~10,000 units of fluorescence signal) in the absence of any compound (100%) for calculating relative SHP-1 inhibition induced by the compounds after subtracting the background signal (~500 units of fluorescence signal) of the substrate.

Induction and Detection of Cellular Protein Tyrosine Phosphorylation in Jurkat Cells Jurkat cells in culture medium ($3 \times 10^6$ cells/ml, 1 ml/tube) were treated with agents for designated times at room temperature. After brief centrifuging in a microfuge (4,000 rpm, 2 min), the cell pellet was lysed on ice for 30 min in 100l of cold lysis buffer (1% NP40, 50 mM Tris, pH 7.4, 150 mM NaCl, 20 mM NaF, 0.2 mM $Na_3VO_4$ and 1 mM $Na_3MO_4$) containing a cocktail of proteinase inhibitors (Sigma, 1 tablet/ 10 ml). The lysates were cleared by centrifuging (14,000 rpm, 10 min) in a microfuge at 4° C. to remove insoluble parts, mixed with equal volume of 2×SDS-PAGE sample buffer, boiled for 5 min and analyzed (~$3 \times 10^5$ cells/well) by SDS-PAGE/Western blotting. Relative intensities of phosphotyrosine bands were quantified through densitometry analysis.

Induction and Quantification of Mouse and Human $IFN\gamma^+$ Cells

For induction of mouse primary $IFN\gamma^+$ cells, splenocytes from female C57BL/6J mice (~8-week old, Taconic Farms, Germantown, N.Y.) were prepared as reported previously (21) following an established protocol approved by the Institutional Animal Care and Use Committee (IACUC) of the Cleveland Clinic. The splenocytes were cultured in RPMI 1640 medium supplemented with 10% FCS in the absence or presence of designated agents for 16 hrs in flat-bottom 96-well plates coated with a monoclonal antibody specific for mouse IFNγ (mouse IFNγ ELISPOT Kit, R & D System). The plates were then processed for in situ detection of IFNγ+ cells by ELISA following the manufacturer's procedure. Scanning and counting of IFNγ+ cells in the plates were accomplished using an automatic ELISPOT reader with Immunospot2 software (Cellular Technology Ltd). Mouse splenocytes were also untreated or treated with agents for 16 hrs in culture dishes and then stained with appropriate isotype control antibodies or FICT-labeled anti-CD3 monoclonal antibody (BD) plus PE-labeled monoclonal antibody (BD) for intracellular IFNγ following established procedures. The stained samples were washed 3 times, re-suspended in 200 µl of 1% paraformaldehyde solution and analyzed (20,000 cells/sample) using a BD FACS Caliburs cytometer and WinList software.

For induction of human primary IFNγ+ cells, heparinized peripheral blood samples were obtained by vein-puncture from healthy volunteers following an established protocol approved by the Institutional Review Board (IRB) of Cleveland Clinic. To mimic in vivo drug-exposure, human peripheral blood samples were directly treated with different agents without pre-separation of white blood cells from other blood components. Blood samples (0.1 ml/sample) were mixed with the agents, incubated at 37° C. for 4 hrs, diluted with 5 volumes of hypotonic solution (10 mM Tris, pH 7.4; 10 mM NaCl) to lyse RBC and centrifuged to pellet WBCs. The pellets were washed with hypotonic solution one time, re-suspended in RPMI 1640 medium (10% FCS) and used for ELISPOT assays (Human IFNγ ELISPOT Kit, R & D System) to quantify human IFNγα cells as outlined above.

Animals and Animal Studies

For in vivo induction of pLck-pY394 and IFNγ+ cells in mice, C57BL/6J mice (~8-week old, female, Taconic Farms, Germantown, N.Y.) were treated with PBS or L5 (~1 or 3 mg/kg body weight/daily, s.c.) for 4 days. Spleens were harvested one hour post-treatment on day 4 and processed into splenocytes, which were used for assessing pLck levels by SDS-PAGE/Western blotting and for quantification of IFNγ+ cells by ELISPOT assays. Mice were also treated with L5 (~10 mg/kg body weight, daily, s. c., n=2) to evaluate the toxicity of the compounds in vivo.

To assess L5 anti-tumor activity, C57BL/6J mice or athymic nude mice (~8-week old, female, Taconic Farms, Germantown, N.Y.) were inoculated (s.c.) at the flanks with B16 melanoma cells ($4 \times 10^4$ cells/site). Four days post-inoculation, the mice were treated with PBS (Control) or L5 (~3 mg/kg body weight/daily, Monday-Friday/week, oral gavage). Tumor volume (n=5) was measured during the study period and calculated using the formula for a prolate spheroid. Student's t test was used for assessing the significance of tumor volume differences among differential treatment groups. Mouse viability (daily) and body weights (weekly) were also recorded during the study period. Major internal organs of the mice were inspected visually upon their termination at the end of the experiment. All studies involving mice were approved by the Institutional Animal Care and Use Committee (IACUC) of the Cleveland Clinic.

Results

Identification of SHP-1 Inhibitory Leads from a Library of Drug-Like Small Chemicals To develop novel SHP-1 inhibitors as potential therapeutics, we sought to identify candidate molecules from a commercial library of ~34,000 drug-like small chemical compounds. The library was screened using a rapid in vitro PTPase assay to assess the effects of individual compounds at 10 µg/ml on the catalytic activity of recombinant SHP-1. Library compounds that induced 90% or more inhibition during the screen were obtained individually and evaluated again to verify their SHP-1 inhibitory activities. A total of 29 compounds with verifiable inhibitory activities against recombinant SHP-1 were identified and designated as lead compounds (or leads).

Leads L5 and L6 Increase Tyrosine Phosphorylation of pLck-pY394 in Jurkat T Cells To identify compounds capable of inhibiting intracellular SHP-1 among the leads, the effects of the leads on SHP-1 substrate pLck-pY394 in Jurkat T lymphocytes were determined. This approach was selected based on direct dephosphorylation of pLck-pY394 by SHP-1, the presence of both proteins in Jurkat cells and the role of T cells as the intended targets for SHP-1 inhibitors for inducing anti-tumor immunity. Direct quantification of PTPase activities of SHP-1 immunoprecipitated from leads-treated cells was not feasible (data not shown), probably due to disassociation of inhibitor/SHP-1 complex during immunoprecipitation.

Figure 2:
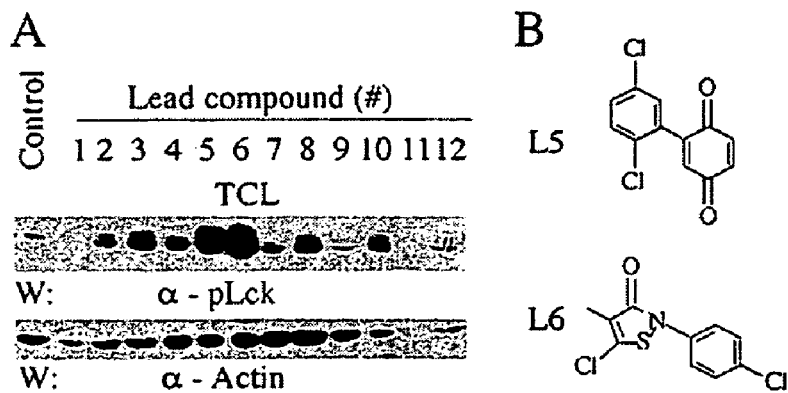
FIG. 2 illustrates differential induction of pLck levels in Jurkat cells by SHP-1 inhibitory lead compounds. A. Jurkat cells in culture were untreated (control) or treated with lead compounds #1 to #12 at 10 min; total cell lysates (TCL) of the cells were prepared and analyzed by SDS-PAGE/Western blotting with antibodies as indicated. Chemical structures of lead compounds #5 and #6.

PLck-pY394 levels in Jurkat cells were induced markedly by lead compounds L5 (~10-fold) and L6 (~14-fold) in comparison to that of the untreated control based on densitometry analysis (FIG. 2A). pLck-pY394 levels were also induced modestly by L3 (~5-fold), L8 (~3-fold) and L10 (~3-fold) (FIG. 2). Minor induction of pLck-pY394 was evident in cells treated by L2 and L4 (<3-fold) (FIG. 2) whereas L1 and L9 failed to induce pLck-pY394 (FIG. 2). In addition, pLckpY394 levels were enhanced (~1-2 folds) by L13-29 under comparable conditions (data not shown).

These results identified L5 and L6 as potent inducer of pLck-pY394 in Jurkat cells and indicated that the two lead compounds of distinct structure (FIG. 2B) were highly effective inhibitors of intracellular SHP-1 PTPase.

Differential Toxicity of L5 and L6 In Vitro and In Vivo

To further characterize L5 and L6, their toxicity was investigated by assessing their effects on the growth of Jurkat T cells in culture and on the viability of mice. SHP-1-specific inhibitors should have little T cell toxicity and limited effect on mouse viability given that SHP-1-deficient mice are viable with developing T cells.

Figure 3:
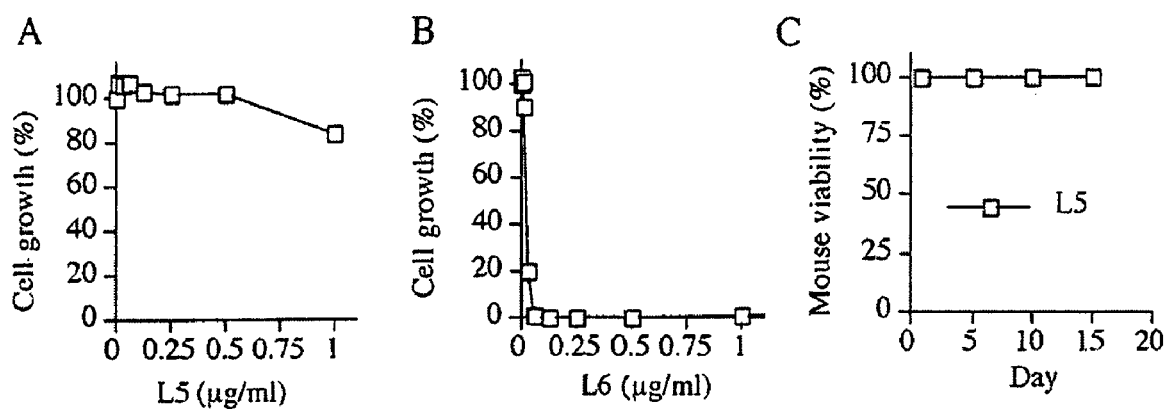
FIG. 3 illustrates differential toxicity of L5 and L6. Jurkat cells were cultured in the absence or presence of lead compound #5 (L5) (A) or #6 (L6) (B) for 6 days prior to quantification of cell growth by MTT assays. Data represent mean±SD of triplicate samples. Balb/c mice were treated with L5 (~10 mg/kg body weight, s. c., daily, M-F/wk) for two weeks to assess its toxicity in vivo (C).

Growth of Jurkat cells in culture were not markedly affected by L5 at doses from ~30 ng-1 µg/ml (FIG. 3A). Under comparable experimental conditions, Jurkat cells in culture were killed completely by L6 at doses from 60 ng/ml to 1 µg/ml and markedly growth inhibited (~80%) by L6 at 30 ng/ml (FIG. 3B). Consistent with the in vitro results, mice treated with L5 (10 mg/kg, daily) for two weeks were all alive (FIG. 3C) and apparently healthy.

These results demonstrated a marked toxicity of L5 against Jurkat cells in culture, suggesting that L6 targeted molecules essential for viability in addition to SHP-1 inhibition. In contrast, L5 had little effects on Jurkat cell growth or mouse viability and apparently targeted SHP-1 in a tolerated manner in vitro and in vivo. Accordingly, L5 was chosen for further characterization described below.

L5 Induces Phosphorylation of SHP-1 Substrates in Jurkat Cells at Low ng Levels

Figure 4:
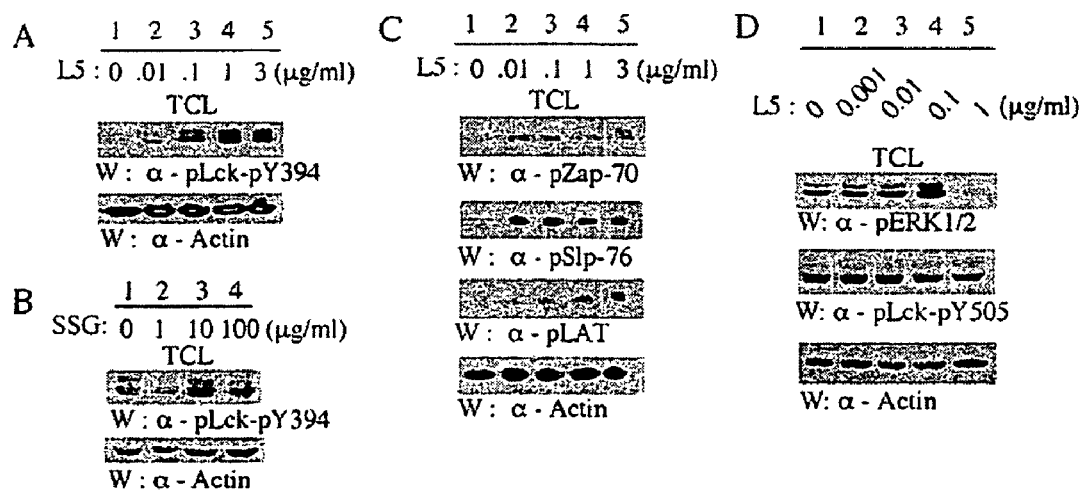
FIG. 4 illustrates L5 increases phosphotyrosine substrates of SHP-1 in Jurkat cells at low ng/ml levels. Jurkat cells were untreated or treated with L5 or SSG at various doses for 10 min. TCL of the cells were prepared and analyzed by SDS-PAGE/Western blotting using antibodies as indicated.

To determine the potency of L5 as an inhibitor of intracellular SHP-1 in T cells was evaluated next, the capacity of L5 at low doses (0.01-3 µg/ml) to induce pLck-pY394 in Jurkat cells was evaluated. Treatment of Jurkat cells with L5 for 10 min in culture induced pLck-pY394 at all of the L5 doses, effective starting at 0.01 µg/ml in a dose-dependent manner (FIG. 4A). pLck-pY394 was induced 2-3-fold by L5 at 0.01 µg/ml and more markedly (>4 folds) at higher doses (0.1, 1 or 3 µg/ml) (FIG. 4A). In contrast, SSG was only effective at 10 µg/ml in inducing pLck-pY394 (~2-fold) but failed at lower (1 µg/ml) or higher (100 µg/ml) doses (FIG. 4B).

To further assess L5 potency against intracellular SHP-1, we investigated L5 effects on pZap70 and pSlp76 that were reportedly dephosphorylated by SHP-1 in T cells as well. The levels of pZap70 and pSlp76 were obviously increased in Jurkat cells treated with L5 at all of the 4 evaluated doses (0.01, 0.1, 1 or 3 µg/ml) (FIG. 4C). Furthermore, L5 also induced pLAT, which functions down stream from pLck during T cell activation.

To assess the effects of L5 on other phosphatases, pERK1/2 and pLck-pY505 in L5-treated Jurkat cells were quantified. SHP-2 is known to be a positive mediator of pERK1/2 whereas pLck-pY505 is dephosphorylated by PTPase CD45. L5 reduced the levels of pERK1/2 at 1 µg/ml but not at lower doses (0.1 to 0.001 µg/ml) and had little effects pLck-pY505 (FIG. 4D).

These results indicated that L5 was a potent and selective inhibitor of intracellular SHP-1 in Jurkat T cells. Capable of inhibiting SHP-1 at low ng level (10 ng/ml, or ~40 nM), L5 was approximately 1,000-fold (or ~350-fold in equal molar ratios) more potent than SSG that was active only at 10 µg/ml (~14 µM). At its effective doses of 10-100 ng/ml for SHP-1 inhibition in Jurkat cells, L5 apparently did not affect SHP-2 or CD45 phosphatases.

L5 Induces Primary IFNγ+ Cells in Mouse Splenocytes and Human Peripheral Blood In Vitro IFNγ+ is a TH1 cytokine expressed in activated anti-tumor immune cells, in which SHP-1 is a key negative regulator. IFNγ+ cells were induced by SSG in its anti-Renca tumor action. As a further step to assess L5, the capacity of the SHP-1 inhibitor to induce primary IFNγ+ cells in mouse splenocytes and human peripheral blood in vitro were evaluated in comparison with SSG.

Figure 5:
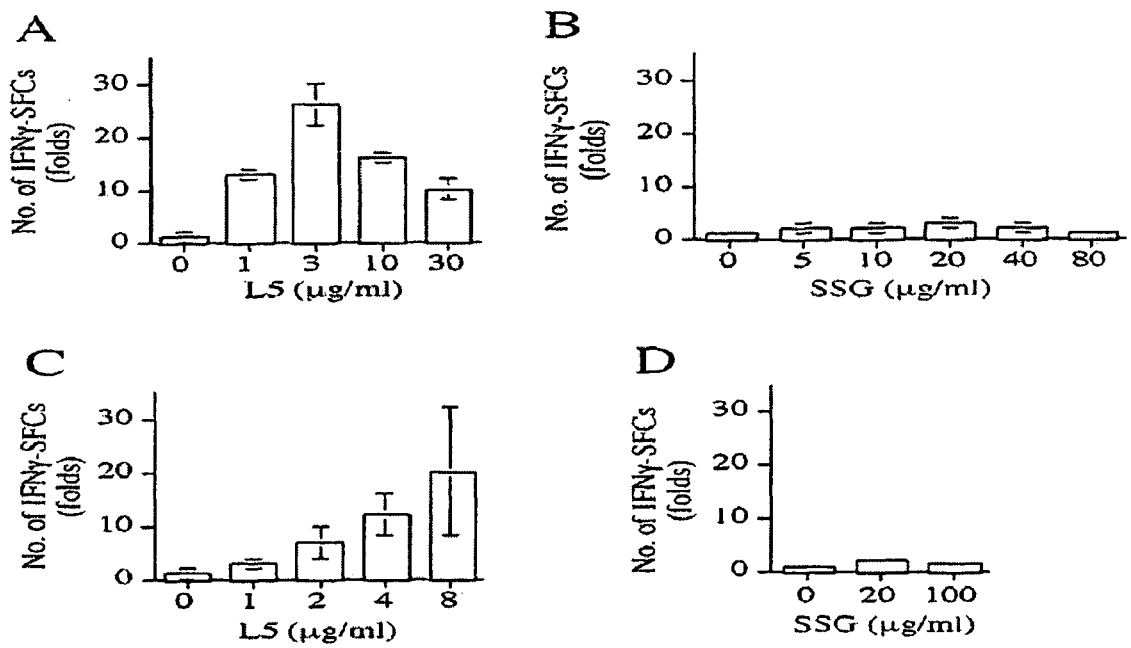
FIG. 5 illustrates L5 induces IFN$^+$ cells in mouse splenocytes in vitro. Relative numbers of IFNγ$^+$ cells in mouse splenocytes or human peripheral blood cultured in the absence or presence of L5 (A) or SSG (B) for 16 hrs as quantified by ELISPOT assays. Data present the mean±SD of duplicate samples.

L5 markedly induced IFNγ+ cells in mouse splenocytes (FIG. 5A) and human peripheral blood (FIG. 5C). IFNγ+ cells were increases in splenocytes treated with L5 at 1 µg/ml (~14-fold), 3 µg/ml (~26-fold), 10 µg/ml (~17-fold) and 30 µg/ml (~10-fold) (FIG. 5A). In contrast, SSG induced maximal increase ~3-fold at its optimal dose (20 µg/ml) (FIG. 5B). IFNγ+ cells in human peripheral blood were also induced by L5 (maximal 20-fold at 8 µg/ml) (FIG. 5C), more effective than SSG (~2-fold at 20 µg/ml) (FIG. 5D).

These results demonstrated that L5 was a potent inducer of mouse and human primary IFNγ+ cells in vitro. When compared with SSG for maximal induction at a comparable dose, L5 was more effective in inducing IFNγ+ cells in mouse splenocytes (~58-fold) and human peripheral blood (~20-fold).

L5 Induces—Mouse Spleen pLck and IFN+ Cells In Vivo

Given the L5 capacity to induce phosphorylation of SHP-1 substrates and to induce IFNγ+ cells in vitro, we next determined whether L5 possessed similar activities in vivo as well. Spleens from mice untreated or treated with L5 were harvested for evaluation of pLck levels and IFNγ+ cells in splenocytes.

Figure 6:
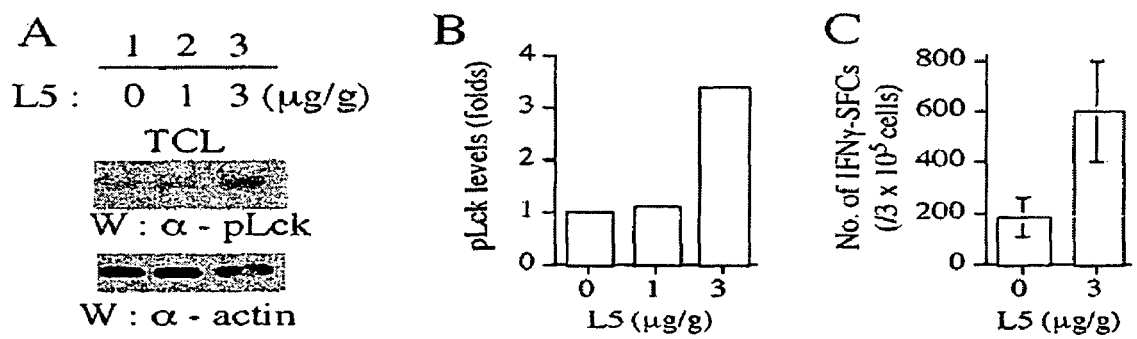
FIG. 6 illustrates L5 induces spleen pLck and IFN$^+$ cells in mice. Mice were untreated or treated with L5 for 4 days (s.c., daily). Splenocytes from the mice were processed into total cell lysates (TCL) and analyzed by SDS-PAGE/Western blotting to detect pLck protein for calculating pLck induction levels (B). The splenocytes were also used in ELISPOT assays to quantify IFNγ$^+$ cells (C, mean±SD of duplicate samples).

Splenocyte pLck was detectable in untreated mice (FIG. 6A, lane 1) and was further increased (~3.3-fold, FIG. 7B) in mice treated with L5 at ~3 mg/kg of body weight (FIG. 5A, lane 3). Spleen IFNγ+ cells were also increased approximately 3-fold (FIG. 6C) in mice treated with a comparable dose of L5. At a lower dose (1 mg/kg of body weight), L5 had only a minor effect on pLck (FIGS. 5A and B) under the experimental conditions. The effects of the low dose of L5 on spleen IFNγ+ cells were not determined.

Consistent with its in vitro activity, L5 thus also induced pLck and IFNγ+ cells in mice, demonstrating that the compound was effective in vivo as well. The reason for the lower levels of L5-induced pLck and IFNγ+ cells in vivo (FIG. 6) in comparison to those in vitro (FIGS. 4 and 5) have not been determined and could be resulted from L5 clearance or metabolism in vivo.

L5 Inhibits the Growth of B16 Melanoma Tumors in Mice

The demonstrated capacity of L5 to induce primary IFNγ+ cells suggests that L5 might have anti-cancer potential given the key role of IFNγ+ cells in anti-tumor immunity. This potential was investigated by assessing the effects of L5, administered orally at 3 µg/g of body weight per day, in C57BL/6 mice bearing 4-day-established B16 melanoma tumors (s. c.). Since L5 had little direct toxicity against B16 cells at doses up to 10 µg/ml (FIG. 7A), the malignant melanoma model would allow detection of L5 anti-tumor effects via immunity in the absence of direct drug actions on cancer cells.

B16 tumors grew aggressively in control mice (FIG. 7B) that had to be terminated by the end of the third week due to large tumor burden and tumor ulceration. Growth of B16 tumors in mice treated with L5 was slower than that of the control, an inhibition detectable when the tumors were visible by the second week (FIG. 7B). At the end of the study, L5 induced ~83% of growth inhibition of B16 tumors in comparison (p<0.002) to that of the control (FIG. 7B). All of the L5-treated mice survived until the end of the study and had no apparent abnormality in behavior or gross anatomy (data not shown).

These results demonstrated a significant anti-B16 melanoma activity for L5 at a tolerated oral dose in mice. The activity was likely mediated via an anti-tumor immune mechanism since the L5 dose lacked direct effects on B16 cell growth but was capable of inducing key anti-tumor immune cells in vivo. In further support, B16 melanoma tumors in athymic nude mice with T-cell-deficiency were not inhibited by L5 under comparable experimental conditions, indicating a requirement of functional T cells for the anti-B16 tumor action of the compound.

Example 2

Identification of Analogs of SHP-1 Inhibitor L5 with Improved Activity in Inducing IFNγ+ Cells and in Growth Inhibition of B16 Melanoma Tumors L5 and SSG are SHP-1 inhibitory agents with anti-cancer potential identified in our recent studies. SSG is an anti-leishmania drug and has been used for decades with undefined mechanism of action. It was found to selectively inhibit SHP-1 PTPase, which negatively regulates anti-tumor immune cells. Furthermore, it showed anti-renal tumor activity in synergy with IL-2 via activating TH1 cells (IFNγ+ T cells) in mice, leading to its early phase clinical trials as a novel anti-cancer agent. Prompted by the encouraging results of SSG, L5 was identified from a library of drug-like small chemicals. Compared to SSG, L5 had increased potency in SHP-1 inhibition, IFNγ+ cell induction and growth inhibition of melanoma tumors in mice. In contrast to obligatory SSG delivered by injection, L5 had additional advantage in its effectiveness as an oral agent that could facilitate its translation into clinical applications. Being a small organic compound of defined structure, L5 might also have potential as a lead compound for developing more refined PTPase inhibitors through chemical modifications.

In this work, chemical analogs of L5 were identified and characterized regarding their activities in SHP-1 inhibition, immune cell activation and pre-clinical anti-tumor action. Our results identified five L5 analogs (L5a1-5) as novel SHP-1 inhibitors with improved activity and defined a benzo-1,4-quinone structure conserved among L5 and L51-5 as a pharmacore essential for the SHP-1 inhibitors. These findings provide further evidence supporting targeting PTPases as an anti-cancer strategy and designate L5 and its analogs as promising compounds for developing PTPase-targeted therapeutics.

Materials and Methods

Cells, Cell Culture and Reagents

Recombinant protein of SHP-1 PTPase catalytic domain was described previously and stored in Tris buffer (25 mM Tris, pH7.5, 1 mM EDTA, 2 μM 2-ME, 25% glycerol) at −80° C. Fluorescence substrate DIFMUP (6,8-difluoro-4 methylumbelliferyl phosphate) was purchased (Molecular Probes). L5 and L5 analogs (Chembridge), mouse IFNγ ELISPOT Kit (R & D System) and antibody against pLck-pY394 (Cell Signaling) were purchased from commercial sources. Human Jurkat T cell line and murine B16 melanoma cell line (ATCC) were maintained in DMSO culture medium supplemented with 10% fetal calf serum (FCS).

Screening of Chemical Databases and Inhibition of Recombinant SHP-1 In Vitro

L5 analogs were identified from chemical databases by computer-assisted structure analysis. Briefly, chemical structure of L5 was compared to individual structures in commercial chemical databases (Chembridge, Mass.; Asinex, N.C.) of approximately one million small organic compounds, utilizing the computers and software at the commercial sites for calculating structural similarities with L5. Compounds with similarities at or above 80% were selected for down-loading structures, which were visually examined and divided into three groups based on key structural features. Ten analogs representing the three groups of compounds were chosen and purchased from commercial source (Hit2Lead, MA) for this work.

To evaluate their SHP-1 inhibitory activity, the analogs (1 μg/well in 0.2 μl DMSO) were aliquot individually to 96-well plates (Falcon, 353072) and mixed with recombinant SHP-1 protein (0.1 μg/well) in 90 μl of HEPES buffer (50 mM HEPS, pH 7.5, 150 mM NaCl, 1 mM EDTA, 0.2 mM DTT and 0.1 mg/ml BSA). The plates were incubated at room temperature for 10 minutes prior to the addition of fluorescence substrate DIFMUP (40 μM stock in HEPES buffer, 10 μl/well) to initiate PTPase reaction. Upon completion of PTPase reaction at room temperature for 1 hr in darkness, fluorescence signal of individual wells were recorded using a Vector$^2$ Multilabel Counter (Vector, CA). They were compared to that of control SHP-1 PTPase reaction (~10,000 units of fluorescence signal) in the absence of any compound (100%) for calculating relative SHP-1 inhibition induced by the compounds after subtracting the background signal (~500 units of fluorescence signal) of the substrate.

To determine if L5 and its analogs might have potential as novel anti-cancer agents with activity superior to SSG based on the significantly higher activities of L5 in inhibiting intracellular SHP-1 and activating immune cells in human peripheral blood in vitro. Accordingly, FIG. 8 illustrates a strategy for developing L5 as a potential anti-cancer agent.

To identify compounds among L5 and its analogs that are capable of activating anti-tumor immune cells in vitro in association with SHP-1 inhibition, the activities of the molecules to (1) induce pLck in Jurkat cells and thymocytes of SHP-1-deficient mice and (2) induce IFNγ+ cells in human peripheral blood in vitro are tested.

Induction and Detection of Cellular Protein Tyrosine Phosphorylation in Jurkat Cells Jurkat cells in culture medium ($3 \times 10^6$ cells/ml, 1 ml/tube) were treated with agents for designated times at room temperature. After brief centrifuging in a microfuge (4,000 rpm, 2 min), the cell pellet was lysed on ice for 30 min in 100 μl of cold lysis buffer (1% NP40, 50 mM Tris, pH 7.4, 150 mM NaCl, 20 mM NaF, 0.2 mM $Na_3VO_4$ and 1 mM $Na_3MO_4$) containing a cocktail of proteinase inhibitors (Sigma, 1 tablet/10 ml). The lysates were cleared by centrifuging (14,000 rpm, 10 min) in a microfuge at 4° C. to remove insoluble parts, mixed with equal volume of 2×SDS-PAGE sample buffer, boiled for 5 min and analyzed (~$3 \times 10^5$ cells/well) by SDS-PAGE/Western blotting as described previously (23, 24). Relative intensities of phosphotyrosine bands were quantified through densitometry analysis.

Induction and Quantification of Mouse IFNγ+ Cells

For induction of mouse primary IFNγ+ cells, splenocytes from female C57BL/6J mice (~8-week old, Taconic Farms, Germantown, N.Y.) were prepared as reported previously (18) following an established protocol approved by the Institutional Animal Care and Use Committee (IACUC) of the Cleveland Clinic. The splenocytes were cultured in RPMI 1640 medium supplemented with 10% FCS in the absence or presence of designated agents for 16 hrs in flat-bottom 96-well plates coated with a monoclonal antibody specific for mouse IFNγ (mouse IFNγ ELISPOT Kit, R & D System). The plates were then processed for in situ detection of IFNγ+ cells by ELISA following the manufacturer's procedure. Scanning and counting of IFNγ+ cells in the plates were accomplished using an automatic ELISPOT reader with Immunospot2 software (Cellular Technology Ltd).

Splenocytes from mice untreated or treated with L5a2 were stained with appropriate isotype control antibodies or FICT-labeled anti-CD3 monoclonal antibody (BD) plus PE-labeled monoclonal antibody (BD) for intracellular IFNγ following established procedures. The stained samples were washed 3 times, re-suspended in 200 μl of 1% para-formaldehyde solution and analyzed (20,000 cells/sample) using a BD FACS Caliburs cytometer and FlowJoe software.

Animals and Animal Studies

To assess anti-tumor activity, C57BL/6J mice (~8-week old, female, Taconic Farms, Germantown, N.Y.) were inoculated (s. c.) at the flanks with B16 melanoma cells ($4 \times 10^4$ cells/site). Four days post-inoculation, the mice were treated with PBS (Control) or L5a2 or L5 (1 mg/kg body weight/ daily, Monday-Friday/week, oral gavage). Tumor volume (n=5) was measured during the study period and calculated using the formula for a prolate spheroid. Student's t test was used for assessing the significance of tumor volume differences among differential treatment groups. Mouse viability (daily) and body weights (weekly) were also recorded during the study period. Major internal organs of the mice were inspected visually upon their termination at the end of the experiment. All studies involving mice were approved by the Institutional Animal Care and Use Committee (IACUC) of the Cleveland Clinic.

Results

Figure 9:
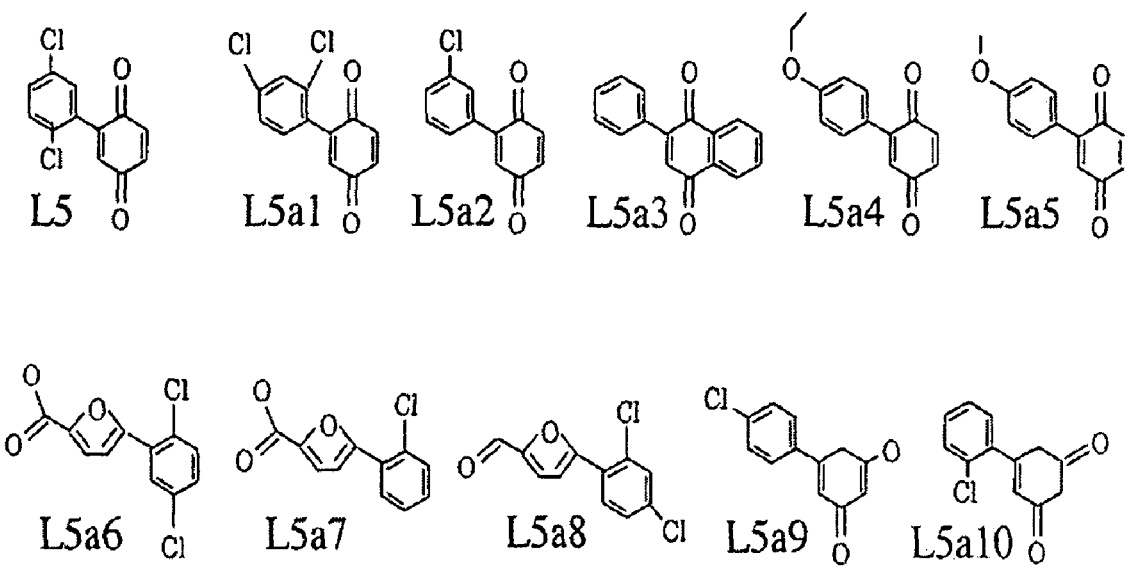
FIG. 9 illustrates chemical structures of L5 and L5 analogs identified through computer-assisted structural analysis. The benzol-1.4 quano core of the compounds is also illustrated.

Identification of L5 Analogs by Computer-Assisted Analysis of Digital Databases of Chemical Structures To identify L5 analogs, digital databases of chemical structures of approximately 1,000,000 compounds were subjected to computer-assisted chemical structure analyses. 84 small chemicals with substantial structural similarities (80% and above) to L5 were identified (data not shown). These chemicals were of three subgroups based on the distinct variations in their related core structures, represented by the 10 analogs (L5a1-10) that were selected for further characterizations (FIG. 9).

L5 Analogs have Differential Activities on SHP-1 Substrate pLck-pY394 in Jurkat Cells in Association with a Benzo-1, 4-Quinone Structure To identify analogs capable of inhibiting intracellular SHP-1, the effects of the analogs on pLck-pY394 in Jurkat T lymphocytes were determined since pLck-pY394 is a substrate directly dephosphorylated by SHP-1 in T cells. Jurkat T cells in culture were treated briefly (10 min) with individual analogs or L5 prior to quantification of intracellular pLck-pY394 levels.

Figure 10:
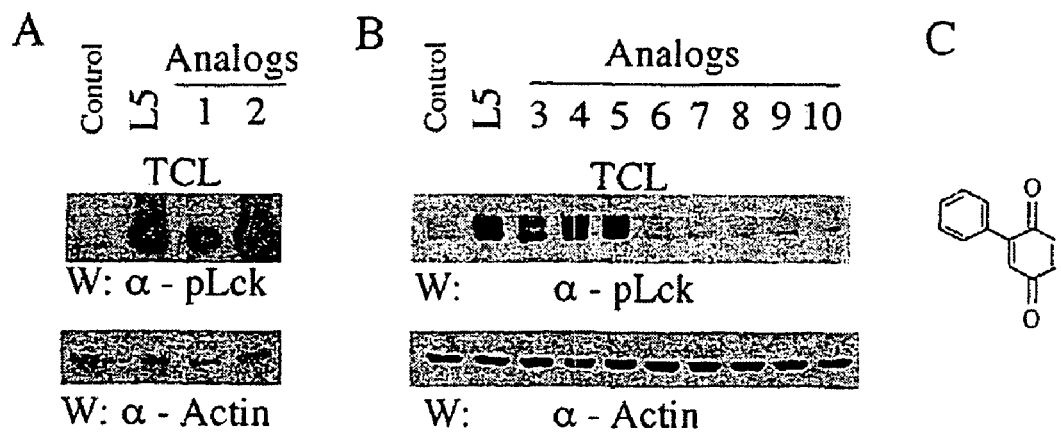
FIG. 10 illustrates differential activities of L5 analogs in inducing pLck in Jurkat T cells. A and B. Total cell lysates (TCL) of Jurkat cells g/ml, 10 min) were analyzed SDS-PAGE/Western blotting with antibodies as indicated. C. Structure of benzo-1,4-quinone presented in L5 and L5a1-5 but not in L5a6-10.

L5a1-5 increased pLck-pY394 levels in Jurkat cells whereas the other L5 analogs (L5a6-10) had little effects (FIG. 10). Based on the levels of pLck-pY394 induced by the compounds, L5a2-5 had comparable or modestly higher activity than L5 while L5a1 was ~50% effective (FIG. 10). From correlative analysis of the chemical structures and the activity to induce pLck-pY394-pY394, a benzo-1,4-quinone structure (FIG. 10C) was found to present in L5 and the active analogs (L5a1-5) but not in the inactive analogs (L5a6-10) (FIG. 9).

These results identified L5a1-5 as potent inducers of pLck-pY394 in Jurkat cells, indicating that they were effective inhibitors of intracellular SHP-1 PTPase in Jurkat T cells. Moreover, benzo-1,4-quinone was identified as a core structure uniquely conserved in the compounds capable of inducing pLck-pY394 and likely required for SHP-1 inhibition.

L5a1-5 are More Potent than L5 in Inducing Mouse Spleno-IFNγ+ Cells In Vitro

IFNγ+ cells are activated anti-tumor immune cells that are negatively regulated by SHP-1. As a further step to evaluate the analogs as potential SHP-1-targeted anti-cancer agents, their activities to induce primary IFNγ+ cells in mouse splenocytes in vitro were determined in comparison with L5.

Figure 11:
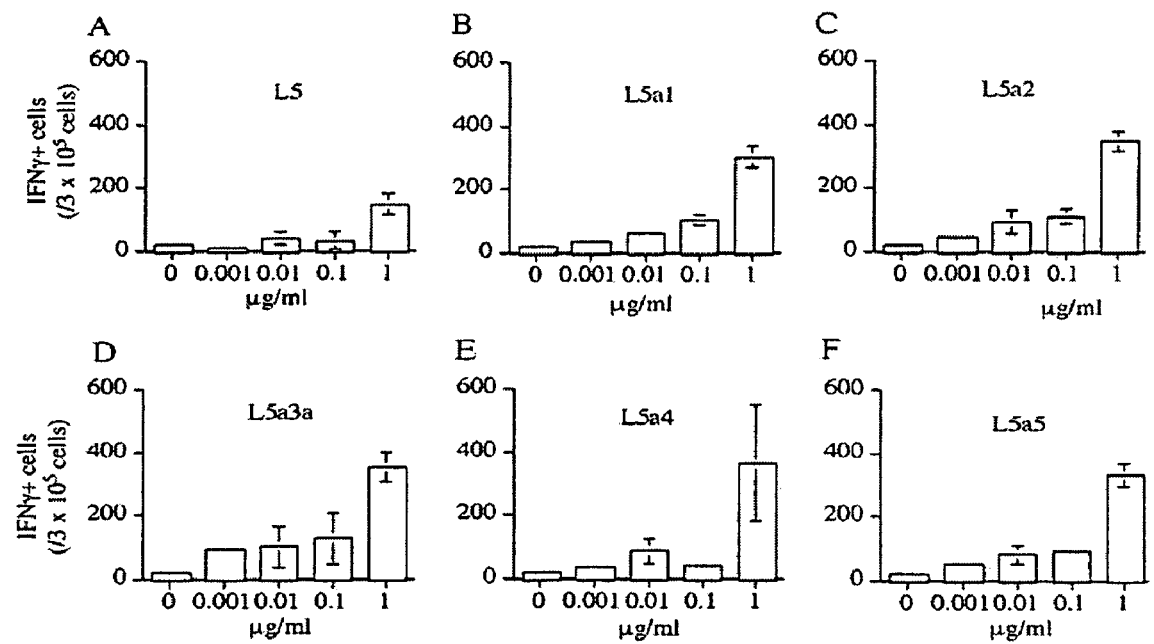
FIG. 11 illustrates L5 analogs are more effective than L5 in inducing mouse spleno-IFN cells in vitro. Splenocytes of C57BL/6 mice were cultured in the absence or presence of L5 or its analogs for 16 hrs.+ cells were□The numbers of IFN quantified by ELISPOT assays. Data represent mean±SD for replicate samples.

L5a1-5 induced mouse spleno-IFNγ+ cells in a dose-dependent manner and was ~2 times more potent than L5 under comparable conditions (FIG. 11). L5 was effective in inducing IFN+$^+$ cells at 0.01 to 1 μg/ml but was inactive at a lower dose (0.001 μg/ml) (FIG. 11A). L5a1-5 were more potent than L5, inducing + cells were induced significantly (~2-3 fold) at 0.001 μg/ml (FIGS. 11B-F). The analogs were also generally about twice more effective than L5 at higher doses from 0.01 to 1 μg/ml (FIG. 11B-F).

Inhibition of Recombinant SHP-1 by the L5+ Cells but not by the Inactive Analogs Active in Inducing pLck-pY394 and IFN Analogs Upon the finding of marked activity for the L5a1-5 analogs in inducing pLck-pY394 and IFNγ+ cells, we investigated whether they were SHP-1 inhibitors like L5 and thus target SHP-1 as a mechanism of action. The effects of these analogs on the phosphatase activity of recombinant SHP-1 in vitro were determined. The analog L5a10 was also included as a key control. Despite its close structure similarity to L5a1-5 (FIG. 9), L5a10 failed to induce pLck-pY394 (FIG. 10B). An SHP-1-dependent mechanism predicted SHP-1 inhibitory activity for L5a1-5 but not for L5a10. Furthermore, it also suggested a lack of activity for L5a10 to induce IFNγ+ cells.

The phosphatase activity of recombinant SHP-1 was completely or almost completely inhibited by L5a1, 2, 4 and 5 (FIG. 12A), similar to the effects of L5 under comparable conditions (FIG. 12A). L5a3 was less effective but still induce ~80% of inhibition (FIG. 12A). In contrast, L5a10 had little effects (~5%) on SHP-1 activity (FIG. 12A). Interestingly, L5a10 induced only low levels (~2-folds in average) of mouse spleno-IFNγ+ cells in vitro at doses from 1-30 μg/ml (FIG. 8B) in comparison to the marked induction (~20-fold) of IFNγ+ cells by L5a1-5 at 1 μg/ml (FIG. 11B-F).

These results identified L5a1-5 as SHP-1 inhibitors similar to L5. Importantly, a correlation was established between SHP-1 inhibition, pLck-pY394 induction and IFNγ+ cell induction for the analogs, which apparently functioned through inhibiting SHP-1 to induce pLck-pY394, leading the induction of IFNγ+ cells.

L5a2 Inhibits the Growth of B16 Melanoma Tumors in Mice at a Tolerated Oral Dose and is More Effective than L5

Since IFNγ+ cells are activated immune cells important in anti-tumor immunity, L5a1-5 might have anti-tumor activity better than that of L5 given their higher potency in inducing IFNγ+ cells (FIG. 11). L5a2 was selected among the analogs for evaluation of anti-tumor activity in comparison with L5 in mouse B16 melanoma tumor model. Like L5, L5a2 failed to inhibit B16 melanoma cells in culture (FIG. 13C). The absence of direct cyto-toxicity against B16 cells would allow sensitive detection of anti-tumor activity mediated by immune cells. C57BL/6 mice bearing 4-day-established B16 melanoma tumors (s. c.) were treated with L5a2 or L5 at a comparable dose (1 mg/kg body weight) through oral gavage.

B16 tumors grew aggressively in control mice (FIG. 13A) that had to be terminated by day 22 due to large tumor burden and tumor ulceration in consistence with previous reports. The growth of B16 tumors in mice treated with L5a2 was inhibited (FIG. 13A), approximately ~75% (p<0.0001) in comparison to the control (FIG. 13B). Under comparable conditions, L5 induced ~9% of tumor growth inhibition that was statistically insignificant (p<0.56) (FIG. 13B). All of the mice treated with L5a2 or L5 survived till the end of the study and had no apparent abnormality in behavior or gross anatomy (data not shown).

These results demonstrated that L5a2 at a tolerated oral dose had anti-B16 melanoma activity more potent than that of L5, suggesting that the other L5 analogs (L5a1, 3, 4 and 5) more potent than L5 in inducing IFNγ+ cells (FIG. 11) might also have improved anti-tumor activity. The anti-tumor activity of L5a2 was likely mediated via an immune mechanism given the lack of a direct growth inhibition of the analog against the melanoma cells. In comparison to our prior study that detected growth inhibition of B16 tumors by L5 at 3 mg/kg, the failure of L5 at 1 mg/kg (FIG. 13) indicated a dose-related anti-tumor action for this compound.

L5a2 Induces Mouse Spleno-IFNγ+ Cells in Vivo

To gain further insights into the mechanism of action in L5a2 in vivo, spleens were harvested from the B16 tumor mice in the control and the L5a2-treated groups (FIG. 13A) on day 22 to assess whether L5a2 induced IFNγ+ cells in the tumor-bearing mice. It was also determined whether the induced-IFNγ+ cells were of CD3+ T lymphocytes, which were activated TH1 critical for anti-tumor immunity. Splenocytes were prepared and co-stained for intracellular IFNγ and the T cell surface marker CD3 for quantification of IFNγ+ T cells by flow cytometry.

Figure 12:
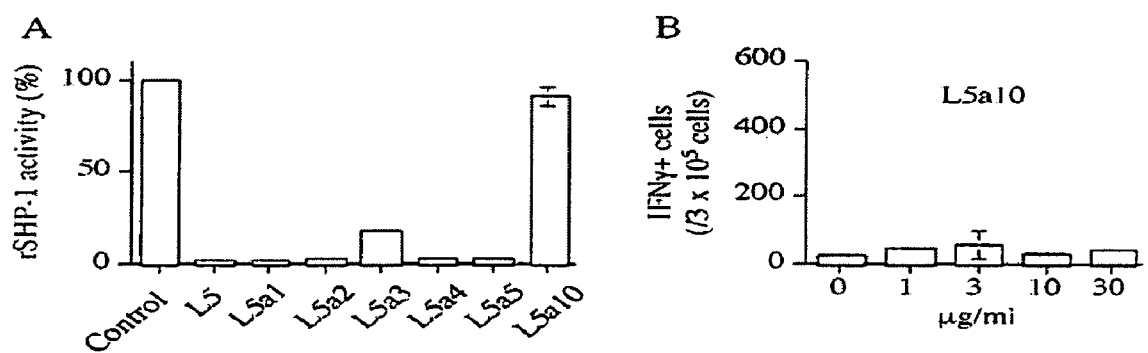
FIG. 12 illustrates correlation of the activities of L5 and analogs in SHP-1+ cell, pLck induction and IFNγ+ cell induction A. Relative activities of recombinant SHP-1 PTPase in the absence or g/ml) in vitro. B. Numbers of IFNγ+ cells in mouse splenocytes stimulated with L5a10 quantified by ELISPOT assays. Data represent mean±SD for replicate samples.
Figure 13:
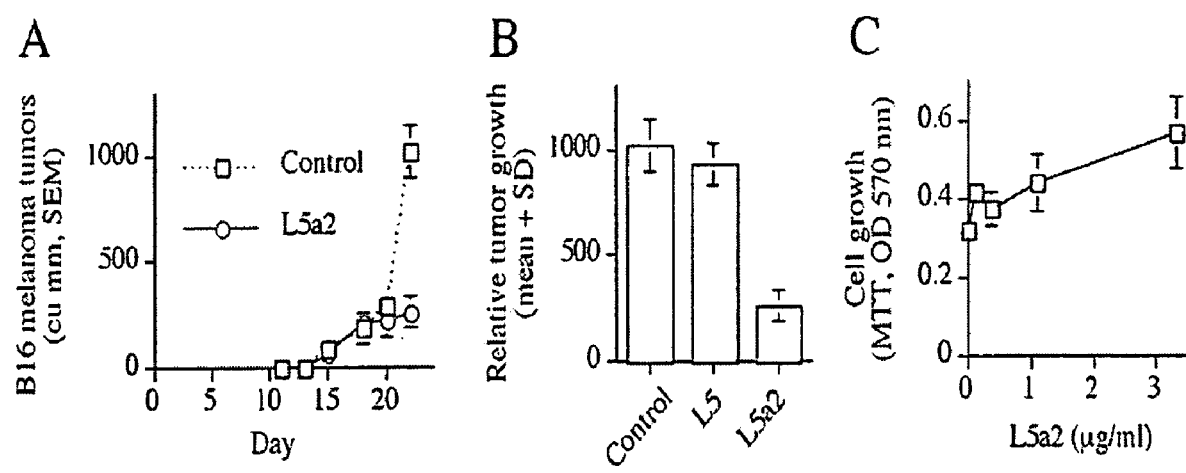
FIG. 13 illustrates L5a2 inhibits the growth of B6 melanoma tumors in mice despite its failure to inhibit B16 cells in culture. A. C57BL/6 mice bearing 4-day-established B16 tumors (s. c.) were untreated (Control) or treated with L5a2 (1 mg/kg/daily, M-F/wk, oral). Data represent mean tumor volume±SEM (n=5). B. Relative tumor growth in control mice and mice treated with L5a2 or L5 on day 22. C. Growth of B16 cells cultured in the absence or presence of L5a2 for 6 days as quantified by MTT assays. Data represent mean±SD for replicate samples.
Figure 14:
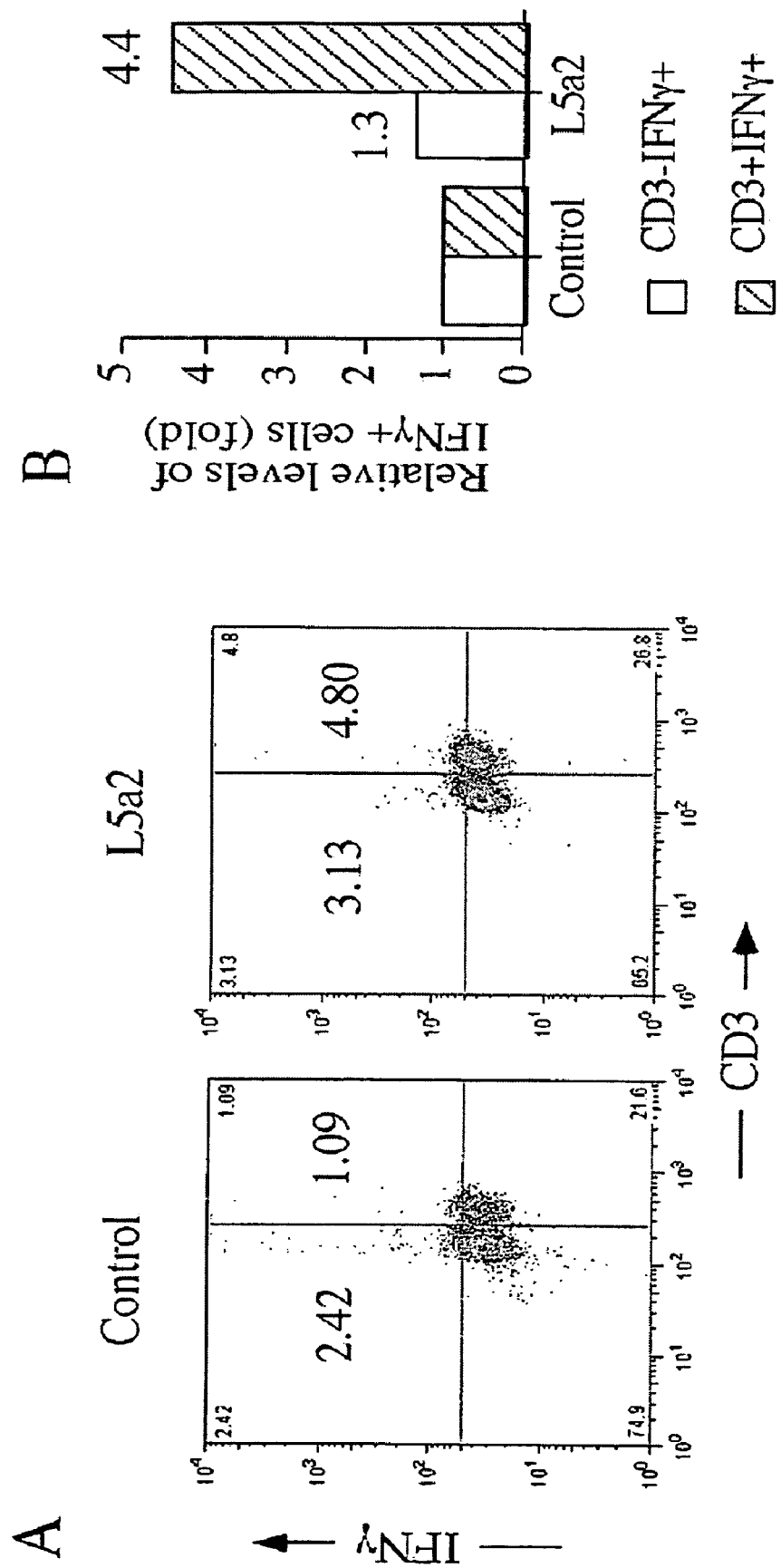
FIG. 14 illustrates induction of IFNγ+ T cell in B16 tumors by L5a2. A. Splenocytes from B16 tumor mice untreated (Control) or treated with L5a2 in FIG. 5 on day 22 were stained for surface CD3 and intracellular IFNγ and subjected to FACS analysis to quantify IFNγ+ cells within CD3+ and CD3− lymphocyte populations. BRelative IFN+ cells (fold) in control and L5a2-treated B16 tumor mice calculated from data in A.

A significant increase of pleno-IFNγ+ cells was evident in L5a2-treated mice in comparison to that of the control and was predominantly within the CD3+ population (FIG. 14). CD3+ IFNγ+ cells were increased ~4.5-fold while CD3- IFNγ+ cells were increased 1.3-fold (FIG. 13B). Consistent with its in vitro activity, L5 thus also induced IFNγ+ cells in mice, demonstrating that the compound was effective in vivo as well. Taken together with the lack of direct growth inhibition of B16 cells by L5a2 (FIG. 13C), these results provide further supporting evidence for anti-tumor mechanism mediated through activating immune cells. It was evident that the levels of L5a2-induced IFNγ+ cells in vivo (FIG. 13B) were lower than those induced by L5a2 in vitro (FIGS. 11 and 12). It had not been determined whether this was resulted from L5a2 clearance in vivo or differential stability of the compound in vivo and in vitro.

Discussion

Lack of clinically usable PTPase inhibitors is a key factor that have hampered the efforts to establish PTPases as cancer therapeutic targets and to develop PTPase inhibitors as new treatments for malignancies and other diseases. Taking advantage of the newly identified SHP-1 inhibitor L5, we sought to develop novel and more potent SHP-1 inhibitors from L5 analogs as potential anti-cancer agents. Our results identified five L5 analogs (L5a1-5) as novel SHP-1 inhibitors more potent than L5 in inducing IFNγ+ immune cells. Moreover, one of the analogs selected for evaluation in mouse models also showed better anti-tumor activity at a tolerated oral dose. These small organic chemical compounds have no previously reported activity or usage to our knowledge.

We provided several lines of evidence demonstrating that L5a1-5 are novel SHP-1 inhibitors with anti-cancer potential and more potent than L5. Capable of inducing primary mouse IFNγ+ cells in consistent with targeting SHP-1, the analogs were approximately 10 times more potent than L5 at low doses and ~2 time at higher doses (FIG. 11). This was demonstrated by their minimal effective dose at 1 ng/ml in comparison to that of L5 at 10 ng/ml and by the heightened IFNγ+ cells induced by the analogs at 0.01-1 μg/ml that were generally 2-fold or more above L5-induced levels (FIG. 11). Consistent with its increased potency in IFNγ+ cell induction, L5a2 also showed improved anti-tumor activity and induced 75% growth inhibition of B16 melanoma tumors that were not affected by L5 under comparable conditions (FIG. 13). The other analogs (L5a1 and L5a3-5) might also have improved anti-tumor activity given their potency comparable to L5a2 in inducing IFNγ+ cells (FIG. 11). We also provided evidence that the anti-tumor activity of L5a2 was likely mediated via an immune mechanism in that L5a2 induced IFNγ+ cells in the tumor mice (FIG. 13) and lacked direct toxicity against B16 cells in culture (FIG. 13C). Such a mechanism of action is consistent with targeting SHP-1, a notion further supported by the capacity of the analogs to inactivate recombinant SHP-1 (FIG. 12A) and to increase SHP-1 substrate phosphorylation (pLck-pY394) in Jurkat T cells (FIG. 10). Additional supporting evidence is the association of the three activities of the analogs to inhibit SHP-1, induce pLck-pY394 and induce IFNγ+ cells (FIGS. 10 and 12). Indeed, analog L510 lacked the three activities and also failed to inhibit B16 melanoma tumors in mice in a preliminary experiment.

These results suggest that L52a, and the other active analogs, might have significant potential for developing novel therapeutics for malignancies or other indications that will benefit from increased immunity. In this regard, L5a2 has several advantages in comparison to the prior identified SHP-1 inhibitory agent SSG that was only modestly active in inducing pLck-p394 and IFNγ+ cells (~2-fold increase) at optimal doses. In addition to improved potency in SHP-1 inhibition and immune cell activation (~20-fold increase, FIG. 11), L5a2 had significant anti-tumor activity as a single agent (FIG. 13) in contrast to the requirement of SSG for combination with cytokines for better anti-tumor efficacy. The demonstrated effectiveness of L5a2 as an oral agent (FIG. 13) is another attractive feature that will facilitate and expedite its clinical investigations and applications, comparing to SSG that requires daily injection. L5a2 might also be a better candidate when compared with its parental lead L5 given its better activity in inducing IFNγ+ cells (FIG. 11) and against B16 tumors (FIG. 13). Considering its effectiveness/tolerance in mice as an easy to use oral agent, this compound may be suitable for rapid clinical translation to assess its therapeutic potential. Additional investigations are warranted.

Another significant aspect of this work is the establishment of L5 as a valuable lead compound for developing novel SHP-1 inhibitors and the consequent identification of benzo-1,4-quinone as a novel pharmacore of SHP-1 inhibitory compounds, which provides exciting opportunities for mechanistic investigations and for developing PTPase-targeted therapeutics. Since L5 analogs L5a1-5 were SHP-1 inhibitors (FIG. 12) with improved activity in IFNγ+ cell induction (FIG. 11) and anti-tumor action (L5a2) (FIG. 13), our results demonstrate that novel SHP-1 inhibitors with improved features could be developed from chemical modifications of the L5 compound. A number of insights to guide chemical modifications could be derived from the benzo-1,4-quinone pharmacore and the structure-activity relationship revealed by the analogs, including key points in L5 and the analogs that will likely tolerate linkages with additional groups or side chains for desirable features. Such modified compounds could be good candidates for developing into therapeutics since they might retain the characteristics of the parental lead(s), including in vivo tolerance and marked biological activities as orally effective agents that are particularly attractive for clinical uses.

This work also provides evidence supporting a strategy focusing on desirable targeting effects in developing PTPase inhibitory therapeutics. Our results do not exclude the possibility that the analogs might also have activity against other PTPases or functionally overlapping targets. If such an activity exists, it was likely inconsequential since it apparently did not cause significant toxicity or prevent the analogs from targeting SHP-1 to activate immune cells for anti-tumor action. In this regard, it is worth noting that all of the FDA-approved kinase inhibitors for cancer treatment are known to inhibit multiple target kinases. Their clinical successes demonstrate that desirable targeting effects are achievable for kinase inhibitors with limited specificity. They also underline the failed prior efforts for decades to reach target mono-specificity for therapeutic kinase inhibitors that likely have delayed progress in this field at substantial costs. Our work illustrates that SHP-1 inhibitors with anti-cancer potential could be identified by focusing on desirable activity in intracellular SHP-1 inhibition, IFNγ+ cell induction and anti-tumor effects. It suggests that similar approaches might be utilized for developing inhibitors for other PTPases of therapeutic potential. Although not an initial key focus, assessment of target spectrum remains a valuable tool that could help the selection of L5 analogs for further development.

Example 3

Anti-Cancer Potential and Mechanism of Action of L6 and Analogs

L6 was identified in our prior study as a small organic compound with SHP-1 inhibitory activity. In this work, we have evaluated L6 and its analogs regarding their potential and mechanism of action as phosphatases-targeted anti-cancer agents.

Materials and Methods
Cells, Cell Culture and Reagents

L5, L6 and L6 analogs (Chembridge), mouse IFNγ ELISPOT Kit (R & D System) and antibody against pLck-pY394 or pERK1/2 (Cell Signaling) were purchased from commercial sources. Human Jurkat T cell line and murine B16 melanoma cell line (ATCC) and other cancer cell lines were maintained in DMSO culture medium supplemented with 10% fetal calf serum (FCS). The effects of chemical compounds on cancer cell growth in culture were quantified by MTT assays following our established procedures.

Screening of Chemical Databases

L6 analogs were identified from chemical databases by computer-assisted structure analysis. Briefly, chemical structure of L6 was compared to individual structures in commercial chemical databases (Chembridge, Mass.; Asinex, N.C.) of approximately one million small organic compounds, utilizing the computers and software at the commercial sites for calculating structural similarities with L6. Compounds with similarities (~70%) were selected for down-loading structures, which were visually examined and divided into three groups based on key structural features. Six analogs representing the three groups of compounds were chosen and purchased from commercial source (Hit2Lead, MA) for this work.

Induction and Detection of Cellular Protein Tyrosine Phosphorylation in Jurkat Cells Jurkat cells in culture medium ($3 \times 10^6$ cells/ml, 1 ml/tube) were treated with agents for designated times at room temperature. After brief centrifuging in a microfuge (4,000 rpm, 2 min), the cell pellet was lysed on ice for 30 min in 100 μl of cold lysis buffer (1% NP40, 50 mM Tris, pH 7.4, 150 mM NaCl, 20 mM NaF, 0.2 mM $Na_3VO_4$ and 1 mM $Na_3MO_4$) containing a cocktail of proteinase inhibitors (Sigma, 1 tablet/10 ml). The lysates were cleared by centrifuging (14,000 rpm, 10 min) in a microfuge at 4° C. to remove insoluble parts, mixed with equal volume of 2×SDS-PAGE sample buffer, boiled for 5 min and analyzed (~$3 \times 10^5$ cells/well) by SDS-PAGE/Western blotting as described previously (17, 18). Relative intensities of phosphotyrosine bands were quantified through densitometry analysis.

Induction and Quantification of Mouse IFNγ+ Cells

For induction of mouse primary IFNγ+ cells, splenocytes from female C57BL/6J mice (~8-week old, Taconic Farms, Germantown, N.Y.) were prepared as reported previously following an established protocol approved by the Institutional Animal Care and Use Committee (IACUC) of the Cleveland Clinic. The splenocytes were cultured in RPMI 1640 medium supplemented with 10% FCS in the absence or presence of designated agents for 16 hrs in flat-bottom 96-well plates coated with a monoclonal antibody specific for mouse IFNγ (mouse IFNγ ELISPOT Kit, R & D System). The plates were then processed for in situ detection of IFNγ+ cells by ELISA following the manufacturer's procedure. Scanning and counting of IFNγ+ cells in the plates were accomplished using an automatic ELISPOT reader with Immunospot2 software (Cellular Technology Ltd).

Animals and Animal Studies

To assess anti-tumor activity, C57BL/6J mice (~8-week old, female, Taconic Farms, Germantown, N.Y.) were inoculated (s. c.) at the flanks with B16 melanoma cells ($4 \times 10^4$ cells/site). Four days post-inoculation, the mice were treated with PBS (Control) or L6 (1 mg/kg body weight/daily, Monday-Friday/week, oral gavage). Tumor volume (n=5) was measured during the study period and calculated using the formula for a prolate spheroid. Student's t test was used for assessing the significance of tumor volume differences among differential treatment groups. Mouse viability (daily) and body weights (weekly) were also recorded during the study period. Major internal organs of the mice were inspected visually upon their termination at the end of the experiment. All studies involving mice were approved by the Institutional Animal Care and Use Committee (IACUC) of the Cleveland Clinic.

Results

L6 Increases Tyrosine Phosphorylation of SHP-1 Substrates in Jurkat T Cells

To evaluate the potency of L6 as an inhibitor of intracellular SHP-1 in T cells, its effects on tyrosine phosphorylation levels of SHP-1 substrates in Jurkat human T cell line were determined. pLck-pY394, pZap70 and pSlp76 in Jurkat cells treated with L6 at doses of 0.01 to 3 μg/ml were quantified in comparison to controls since they were direct SHP-1 substrates in T cells. Their down-stream signaling molecule pLAT in L6-treated Jurkat cells was also investigated.

Figure 15:
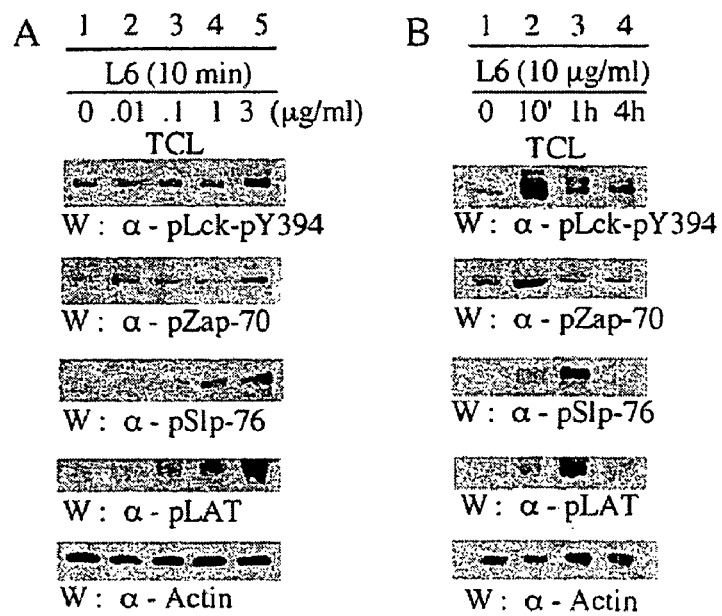
FIG. 15 illustrates L6 increases tyrosine phosphorylation of SHP-1 substrates in Jurkat T cells. Jurkat T cells were treated with L6 at indicated doses and time. Total cell lysates (TCL) were prepared and analyzed by SDS-PAGE/Western blotting with antibodies as indicated.

L6 increased pLck-pY394, pZap70, pSlp76 and pLat in a dose- and time-dependent manner (FIG. 15). L6 induced pLck-pY394 and pZap70 at 3 μg/ml only, induced pSlp76 starting at 1 μg/ml and increased pLAT starting at 0.1 μg/ml after treatment for 10 minutes (FIG. 15A). L6 also induced the phosphotyrosine proteins at 1 hr (pLck-pY394, pSlp96 and pLAT) and 4 hr (pLck-pY394 and pLAT) (FIG. 15B).

These results indicated that L6 was capable of inhibiting SHP-1 in Jurkat cells at microgram and sub-microgram doses for durations up to several hours. The differential effects of L6 on these phospho-proteins was consistent in part with sequential signal amplification given that pLck and pZap70 were up-stream of the other two molecules in the signaling cascade for activating immune cells.

L6 Induces Mouse Spleno-IFNγ+ Cells In Vitro with Potency Superior to L5 at Low Doses Given its inhibition of intracellular SHP-1 (FIG. 15), L6 might be capable of activating immune cells similar to the recently identified SHP-1 inhibitor L5. We therefore evaluated the activity of L6 to induce primary IFNγ+ cells in vitro in comparison to L5. IFNγ+ cells in mouse splenocytes cultured with or without L6 or L5 for 16 hr were quantified by ELISPOT assays.

Figure 16:
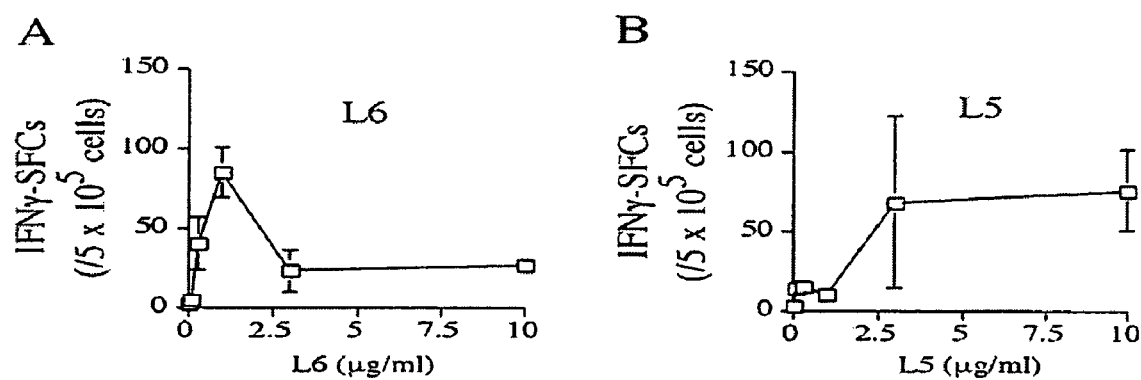
FIG. 16 illustrates L6 induces mouse spleno-IFNγ+ cells in mouse splenocytes cultured in the absence or presence of L6 or L5 for 16 hrs were quantified by ELISPOT assays. Data represent mean±SD of replicate samples.

L6 was a potent inducer of IFNγ+ cells at low doses of 0.3 and 1 μg/ml (FIG. 16A), inducing approximately 10-fold and 22-fold increases respectively. L6 at higher doses (3 or 10 μg/ml) was less effective (FIG. 16A). Under comparable conditions using splenocytes of the same mouse, L5 had limited activity (~3-4 fold induction) at the low doses (0.01 to 1 μg/ml). However, L5 at higher doses induced significant IFNγ+ cells (FIG. 16B).

These results demonstrated L6 activity in inducing IFNγ+ cells that was more potent than L5 at low doses and less effective at higher doses. The lesser activity for L6 at higher doses might be resulted from cyto-toxicity against immune cells as indicated by its killing of Jurkat T cells in culture.

L6 Inhibits B16 Melanoma Tumor Growth in Mice and had Cyto-Toxicity Against Melanoma Cell Lines In Vitro L6 activity to induce IFNγ+ cells suggested an anti-tumor action for the compound since IFNγ+ cells are activated immune cells important in anti-tumor immunity. To assess L6 anti-tumor activity, mice bearing 4-day-established B16 melanoma tumors were treated with the compound (1 mg/kg body weight) for 3 weeks by oral gavage. This L6 treatment was chosen based on its tolerance in mice in a preliminary study (data not shown) and its potential to deliver a vivo dose comparable to the peak effective dose (1 μg/ml) of L6 in inducing IFNγ+ cells (FIG. 16A).

B16 tumor growth was inhibited (~40%) by L6 significantly ($p<0.03$) in comparison to control. The treatment was tolerated with no apparent behavior or gross anatomic abnormalities in the treated mice which all survived till the end of the study (data not shown).

Figure 17:
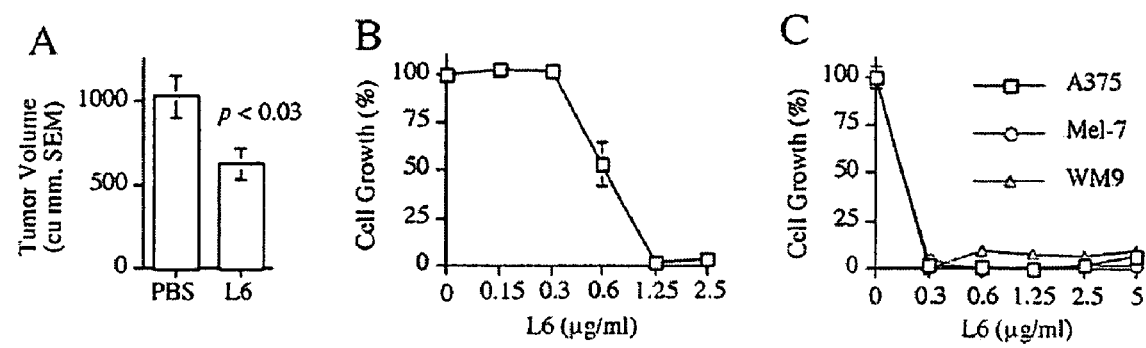
FIG. 17 illustrates L6 inhibits the growth of B16 melanoma tumors in mice and has cyto-toxicity against melanoma cell lines in culture. A, B16 tumor volumes (n=5) in mice treated with PBS or L6 for 3 weeks. B and C, relative numbers of viable cells cultured in the absence or presence of L6 as quantified by MTT assays. Data represent mean+SD of triplicate samples.
Figure 18:
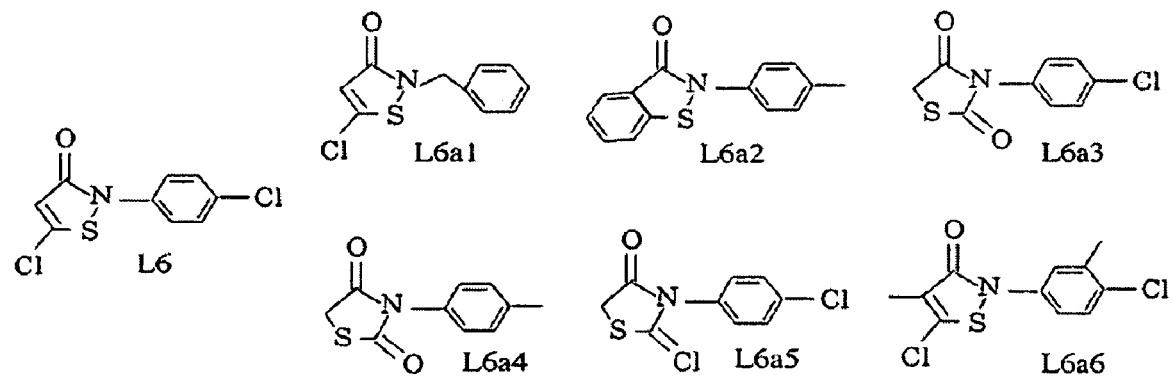
FIG. 18 illustrates L6 analogs identified by computer-assisted structure analysis. Structures of L6 analogs in comparison to L6.

To gain mechanistic insights, the effects of L6 on B16 cell growth in culture was determined to assess whether L6 had cyto-toxicity against B16 cells that could contrite to anti-tumor action. Indeed, L6 was capable of killing B16 melanoma cells in culture at 0.6 μg/ml and above (FIG. 17B). Moreover, L6 was also capable of complete kill of three other melanoma cell lines starting at 0.3 μg/ml in vitro (FIG. 17C).

Figure 20:
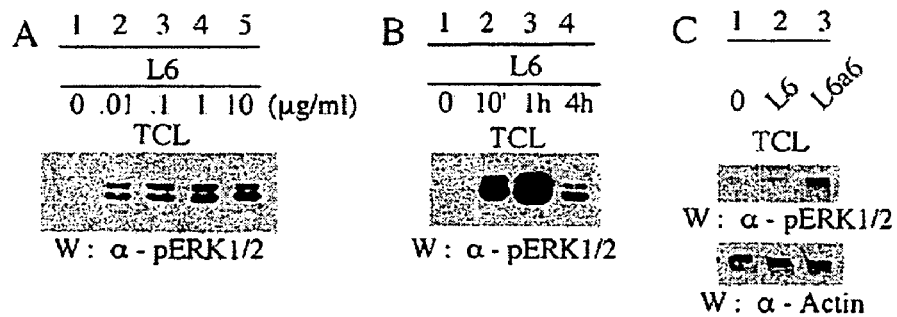
FIG. 20 illustrates L6 induces pERK1/2 in Jurkat and B16 cells. A and B, Western blotting membranes with samples and probed for the SHP-1 substrates were stripped and then re-probed with an antibody for pERK1/2. C, B16 cells were treated with L6 or L6a6 at g/ml for 10 min and subjected to SDS-PAGE/Western blotting to quantify pERK1/2.
Figure 21:
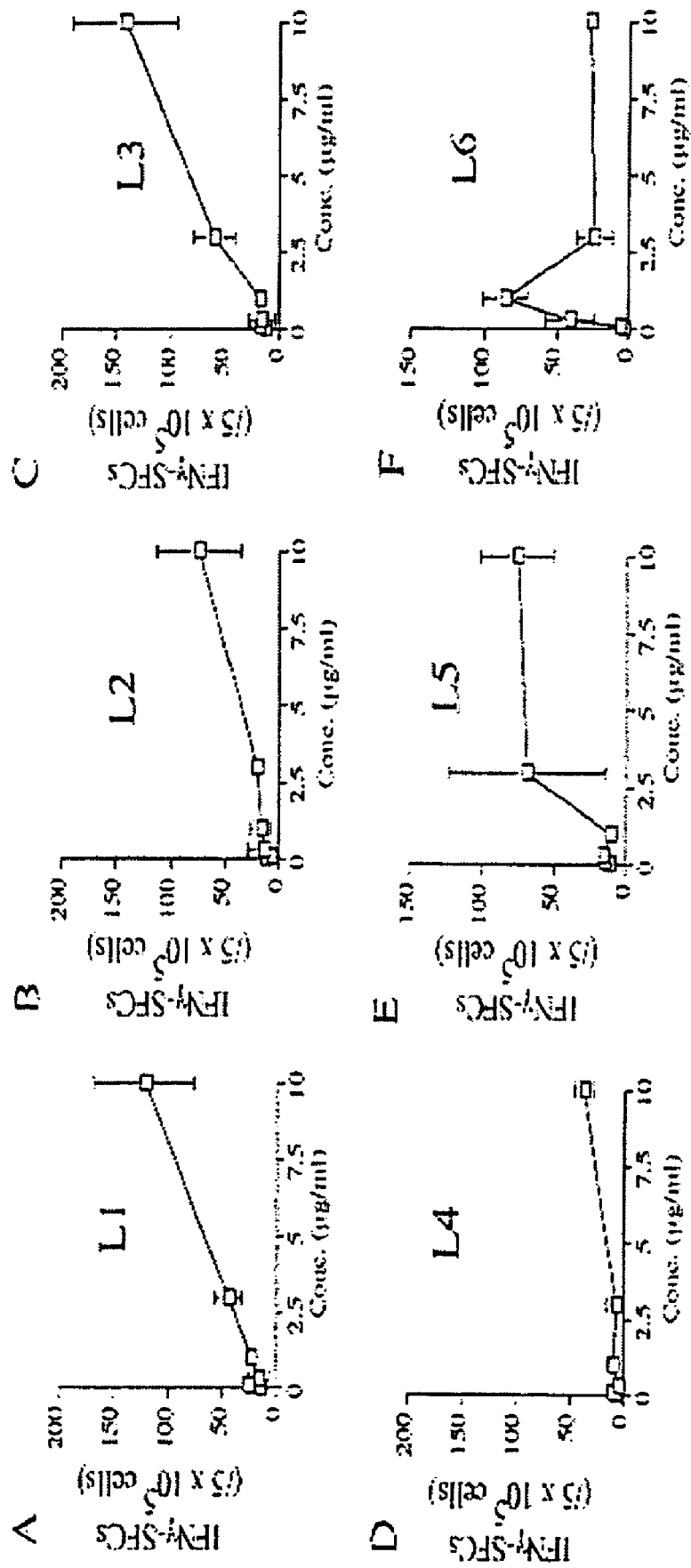
FIG. 21 illustrates comparable activities of L1-6 in IFNγ+ cell induction. Mouse splenocytes were cultured in the absence or presence of the lead compounds at indicated doses for 16 hrs. IFNγ+ cells were then quantified by ELISPOT assays. Data represent mean±SD of replicate samples.

These results demonstrate an anti-B16 tumor activity of L6 at a tolerated oral dose. This anti-tumor activity might be mediated via both an immune mechanism and a direct cyto-toxic effect given the L6 capacity to induce IFNγ+ cells (FIG. 16A) and to directly kill B16 cells (FIG. 20A). Indicating a general anti-melanoma toxicity for the compound, L6 at its anti-tumor dose tolerated in mice was apparently even more effective in killing three other melanoma cell lines (FIG. 17C). Thus, tumors formed by those cell lines in mice might be more responsive to L6 treatment than B16 tumors.

Identification of L6 Analogs with Low and High Cyto-Toxicity Toward Cancer Cell Lines Encouraged by the above results that indicated an anti-cancer potential of L6, we evaluated L6 as a lead compound to develop novel and more potent anti-cancer agents. As an initial step, we identified 48 analogs of L6 by computer-assisted chemical structure analysis of chemical structures of ~one million compounds in two databases. Six representative analogs (L6a1-6, FIG. 4) and L6 were further evaluated for cyto-toxicity against B16 melanoma cells and a panel of cell lines of common malignancies.

Figure 19:
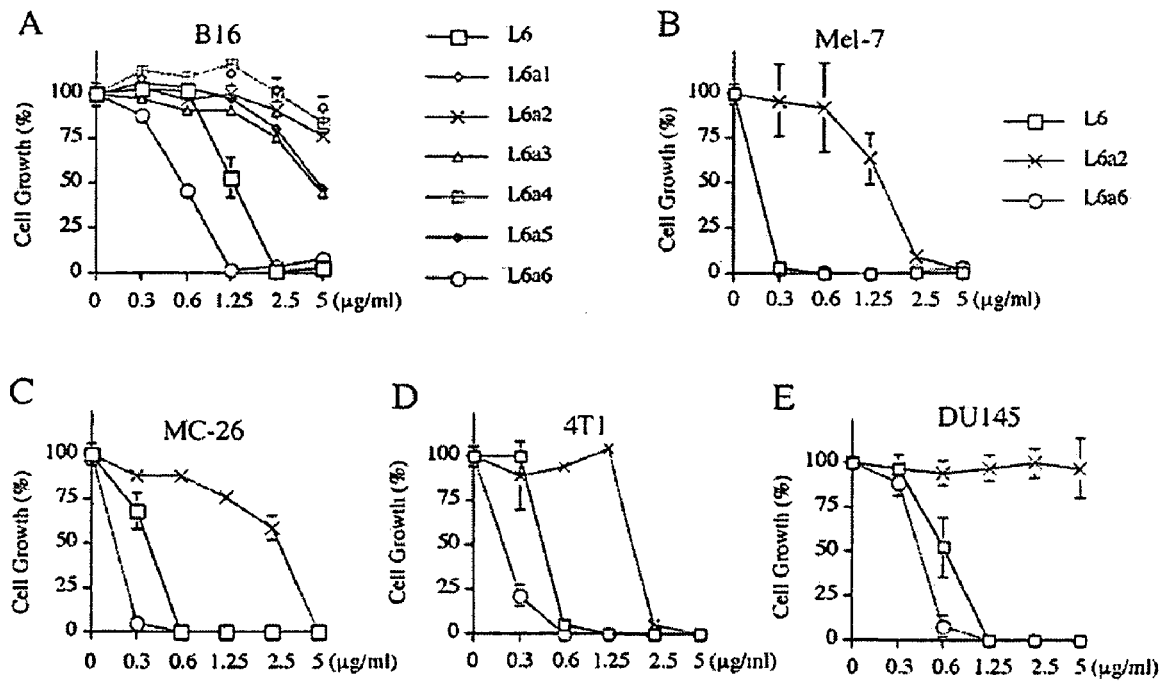
FIG. 19 illustrates L6 and analogs have cyto-toxicity in vitro against cancer cell lines. Cancer cells were cultured in the absence or presence of L6 or L6 analogs and then subjected to MTT assays for quantification of viable cells. Data represent mean±SD of triplicate samples.

The analogs and L6 had differential cyto-toxicity toward B16 cells in culture (FIG. 19A). L6 and L6a2 were highly toxic and completely killed B16 cells at 1.25 and 2.5 μg/ml respectively (FIG. 19A). In contrast, the other analogs (e.g., L6a2) had little or limited toxicity under comparable conditions (FIG. 19A).

L6 and L6a6 were even more toxic when evaluated against four other cancer cell lines, including melanoma MeI-7, colon cancer MC-26, breast cancer 4T1 and prostate cancer DU145. Their effective dose for complete kill against these cells were only 10-50% of those for B16 cells. Chosen to represent the less toxic analogs, L6a2 generally killed the cancer cells at doses ~5-10 folds higher (FIGS. 19B, C and D) and failed to affect DU145 cell growth at the highest testing dose (5 μg/ml) (FIG. 19E).

Induction of pERK1/2 in Cancer Cells by L6 and L6a6 Correlates with the Cyto-Toxicity of the Compounds To investigate the mechanism of action for L6 induced cancer cell death, we determined the effects of L6 on pERK1/2. Prior studies showed that sustained high pERK1/2 could induce growth arrest and apoptosis of cancer cells.

Starting a low dose of 0.01 mg/ml, L6 induced pERK1/2 in Jurkat cells (FIG. 20A). This dose was capable of complete kill of Jurkat cells in culture but had limited effects on intracellular SHP-1 substrates (FIG. 15A). L6-induced pERK1/2 were sustained at a higher level up to 1 hr and then reduced to a level above background by 4 hr (FIG. 20B). L6 also induced pERK1/2 in B16 cells although it was less effective than L6a6 (FIG. 20C), correlating with its lower cyto-toxicity to B16 cells in comparison to the analog (FIG. 20A). The levels of pERK1/2 induced by L6 in B16 cells were lower than those in Jurkat cells (FIGS. 20A and C), indicating a correlation of higher L6 toxicity against Jurkat cells (killing dose=0.01 μg/ml) (26) than B16 cells (killing dose=2.5 μg/ml) (FIG. 19A).

These results demonstrated a pERK1/2-inducing activity for L6 and L6a6, which correlated with the cyto-toxicity of the compounds against malignant cells in culture. Supported by the correlation and the reported role of pERK1/2 in cancer cell growth arrest and death, this activity might mediate the cyto-toxicity of the compounds against the malignant cells. Since pERK1/2 are substrates dephosphorylated by several phosphatases, our results implicated these pERK phosphatases as target molecules of L6 and L6a6 in their cytotoxic action.

Example 4

Induction of IFNγ+ Cells by Lead Compounds L1-4 Suggests their Potential for Developing Phosphatase Inhibitors and Immune Cell Activators for Therapeutic Purposes In recent study, we evaluated 4 additional compounds (L1-4) among the 29 leads in comparison to L5 and L6 regarding their activity in inducing mouse IFNγ+ cells, which are activated immune cells important for immunity against malignancies and infections.

Our results (FIG. w1) demonstrated that L1 and L3 had significant activity comparable to or better than those of L5 or L6, particularly at higher doses. This activity is consistent with their identified activity in SHP-1 inhibition (Table 1). These results suggest that these two leads, and their analogs, might have potential for developing phosphatase inhibitors and immune cell activators for therapeutic purposes.

Example 5

L6 and Analogs are Novel MKP Inhibitors at low nM Levels with Anti-Cancer Potential Selective Inhibition of MKPs by L6 and L6 Analogs at Low nM Levels.

MKPs are phosphatases that selectively dephosphorylate and inactivate MAPKs, including ERK1/2, p38 and JNK. They are also potential cancer therapeutic targets. In particular, MKP1 is a key mediator of drug-resistance in cancer cell and could be targeted to improve therapeutic efficacy. Moreover, targeting MKP1 and several other MKPs could activate JNK and p38, resulting in cancer cell death by apoptosis. Prior efforts by other investigators have identified MKP1 inhibitory compounds that were active at μM levels.

We demonstrated (FIG. 22) that L6 and its analogs were potent inhibitors of MKPs in Jurkat human leukemic cells, increasing phosphorylation of intracellular MKP substrates starting at low levels of 1 ng/ml (~2-10 nM).

Figure 22:
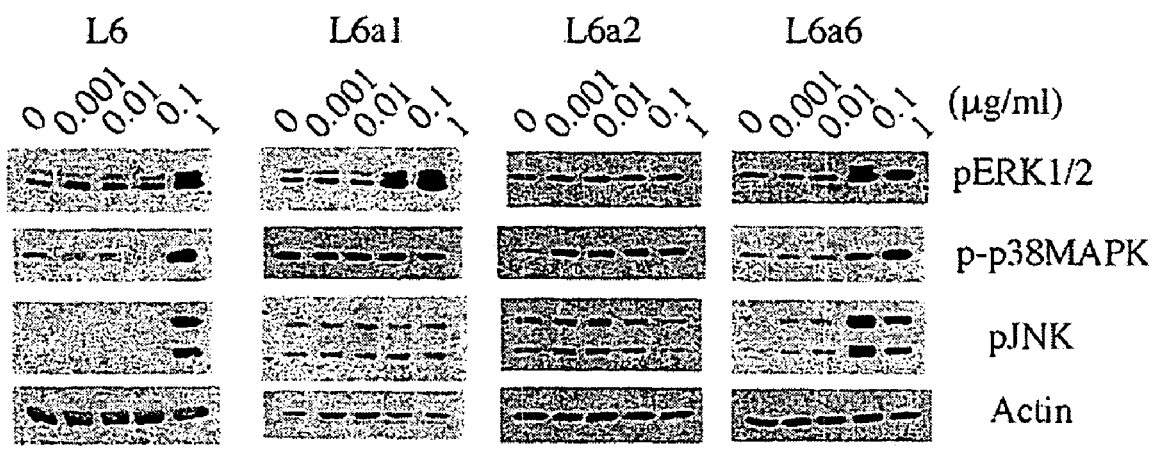
FIG. 22 illustrates selective induction of MKPs substrates by L6 and analogs in Jurkat human leukemic cells. Jurkat cells were treated with the compounds for 30 min in culture prior to quantification of MKPs substrates by SDS-PAGE/Western blotting.

Furthermore, each of the compounds predominantly targeted a selective MKP as indicated by their differential effects on the substrates (FIG. 22). L6 at low doses (1-100 ng/ml) induced pERK1/2 without affecting p38 whereas L6a2 selectively induced p38 phosphorylation. Interestingly, L6a6 induced pJNK and p-p38 starting at 1 ng/ml and markedly at higher doses but induced pERK1/2 only at the high doses.

Thus L6a6 mainly acted against MKP1 dephosphorylate the three MKPs with preference for pJNK and p-p38. L6a1 inhibited HVH3 that dephosphorylates pERK1/2 only. L6a2 targeted a p38-specific MKP. L6 inhibited HVH3 at lower does but had effects on other MKPs at 1 microgram/ml.

L6 and Analogs Induced Jurkat Cell Death by Apoptosis in Correlation with their Capacity to Induce pJNK and p-p38.

Figure 23:
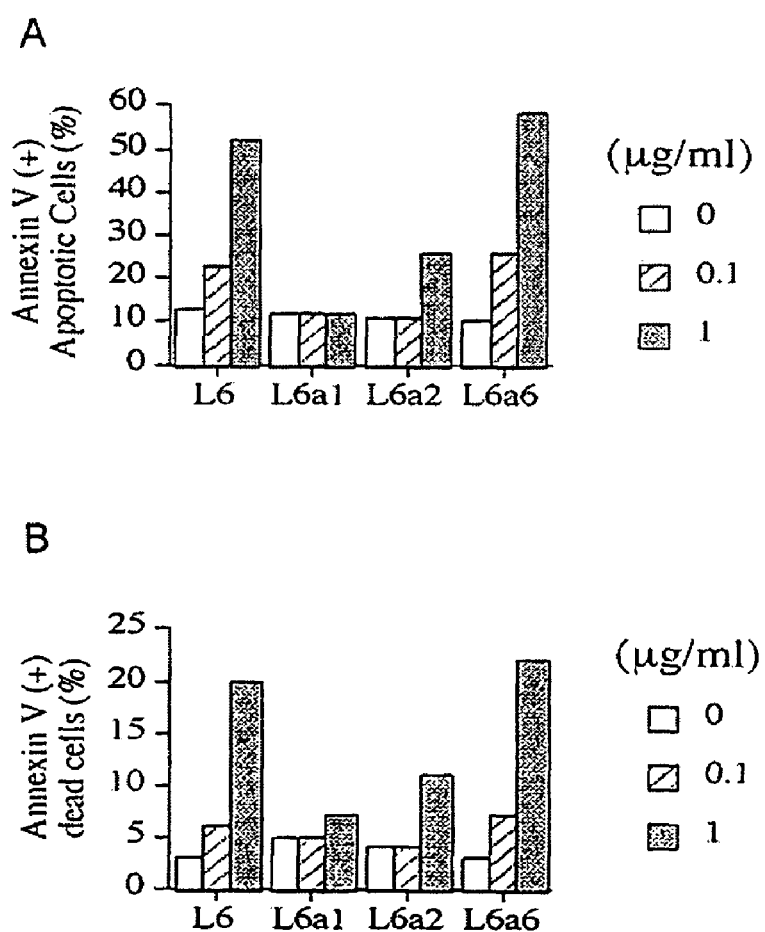
FIG. 23 illustrates jurkat cells were treated with L6 and analogs in culture for 16 hrs. Cells were then stained for apoptotic marker Annexin V and cell death marker 7-AAD prior to FACS analysis.

Providing further evidence of targeting MKPs and indicating their anti-cancer potential, L6 and analogs induced Jurkat cell death by apoptosis in correlation with their capacity to induce pJNK and p-p38. Jurkat cell apoptosis were induced by L6, L6a2 and L6a6 (FIG. 23). The levels of apoptosis were proportional to the pJNK and p-p38 levels induced by the compounds (FIG. 23). L6a1 failed to induce apoptosis, consistent with its lack of activity to induce pJNK or p-p39.

L6 and L6a6 Augment Cytotoxicity of 5FU Against Human Colon Cancer Cells.

Given the role of MKPs in protecting cancer cells from attack by cytotoxic cancer therapeutics, L6 and analogs might synergy with the cancer drugs to improve clinical efficacy through targeting MKPs.

Figure 24:
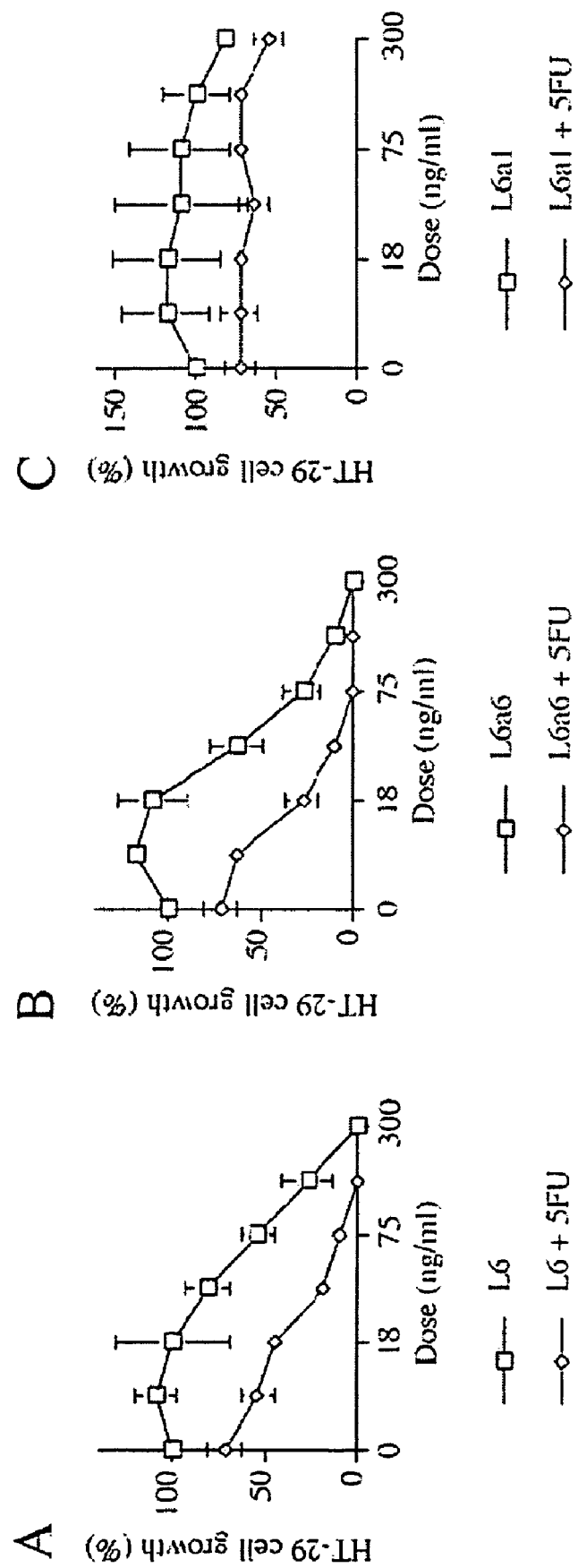
FIG. 24 illustrates HT-29 cells were treated with L6 or the analogs in the absence or presence of 5FU (2 μm) for 3 days. After washing, the cells were cultured for 4 days prior to quantification of viable cells by MTT assays.

This notion is supported by the observation (FIG. 24) that cytotoxicity of cancer drug 5FU against HT-29 human colon cancer cells was augmented by L6 and L6a6, which were capable of inducing pJNK and p-p38 (FIG. 22), but not by L6a1.

From the above description of the invention, those skilled in the art will perceive improvements, changes and modifications. Such improvements, changes and modifications within the skill of the art are intended to be covered by the appended claims. It will be appreciated that references, patents, and publication recited in the application are herein incorporated by reference in their entirety.

Having described the invention, I claim:

1. A method of treating breast cancer, lung cancer, skin cancer, prostate cancer, bladder cancer, pancreas cancer, renal cell carcinomas, leukemias, lymphomas, multiple myelomas, solitary plasmacytoma, extramedullary plasmacytoma, Waldenstrom's macroglobulinemia, monoclonal gammopathy of undetermined significance, benign monoclonal gammopathy, heavy chain disease, bone and connective tissue sarcomas, brain tumors, breast cancer, adrenal cancer, thyroid cancer, pancreatic cancer, pituitary cancers, eye cancers, vaginal cancers, vulvar cancer, cervical cancers, uterine cancers, ovarian cancers, esophageal cancers, squamous cancer, stomach cancers, colon cancers, rectal cancers, liver cancers, gallbladder cancers, cholangiocarcinomas, lung cancers, testicular cancers, prostate cancers, oral cancers, salivary gland cancers, pharynx cancers, skin cancers, kidney cancers, bladder cancer, in a subject, the method comprising:
   administering to the subject an amount of at least one phenyl isothiazolone or analog thereof to the subject effective to inhibit cancer cell growth in the subject, wherein treating cancer in a subject comprises relieving cancer in the subject.

2. The method of claim 1, the phenyl isothiazolone or analog thereof being administered at an amount to inhibit SHP-1 in the subject.

3. The method of claim 1, the phenyl isothiazolone or analog thereof being administered at an amount effective to induce immune cells activation in the subject.

4. The method of claim 1, the phenyl isothiazolone or analog thereof being administered at an amount effective to induce a cytokine response in the subject.

5. The method of claim 1, the cancer cell comprising a tumor cell.

6. The method of claim 1, the phenyl isothiazolone or analog thereof being administered at about 1 μg/kg to about 10 mg/kg to the subject.

7. The method of claim 1, the phenyl isothiazolone or analog thereof comprising at least one of the following formulas:

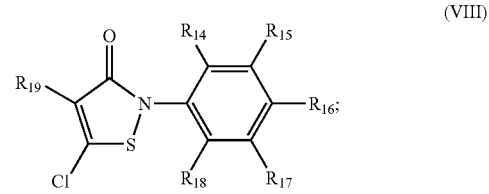

(VIII)

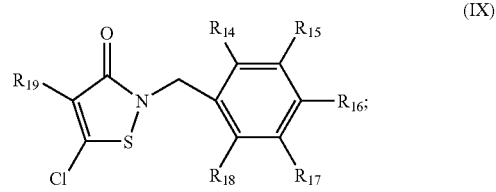

(IX)

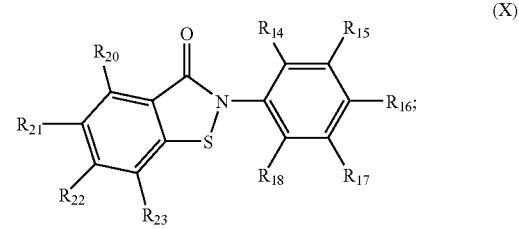

(X)

-continued

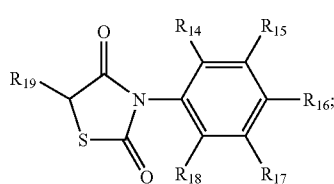
(XI)

where $R_{14}$, $R_{15}$, $R_{16}$, $R_{17}$, $R_{18}$, $R_{19}$, $R_{20}$, $R_{21}$, $R_{22}$ and $R_{23}$ each independently represent substituents selected from the group consisting of hydrogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, $C_2$-$C_{24}$ alkylcarbonyl (—CO-alkyl), $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_{10}$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano(—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino, alkylimino, arylimino, nitro (—NO$_2$), nitroso (—NO), sulfo (—SO$_2$—OH), sulfonato (—SO$_2$—O$^-$), $C_1$-$C_{24}$ alkylsulfanyl (—S-alkyl), arylsulfanyl, $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), phosphino (—PH$_2$), and combinations thereof; or a pharmaceutically acceptable salt thereof.

8. The method of claim 1, the phenyl isothiazolone or analog thereof comprising at least one of the following formulas:

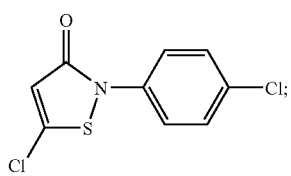
(VIIIa)

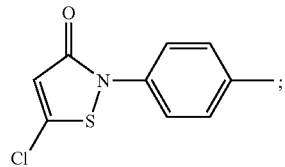
(VIIIb)

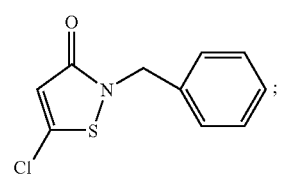
(IXa)

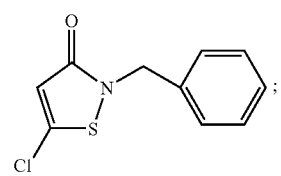
(IXa)

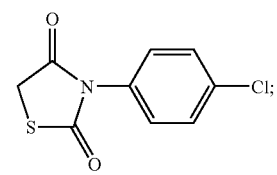
(XIa)

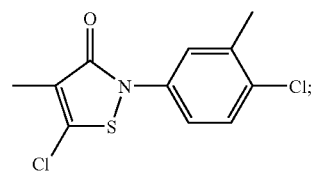
(VIIIc)

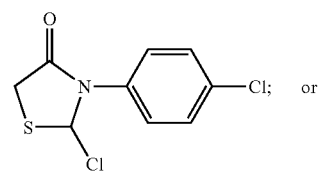
(XIIa)

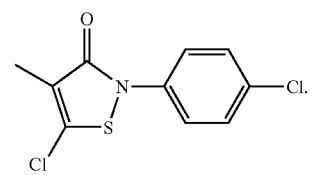
(VIIId)

* * * * *